United States Patent
Kimura

(10) Patent No.: US 8,107,071 B2
(45) Date of Patent: Jan. 31, 2012

(54) METHOD FOR DETECTING MOLECULAR ANALYSIS LIGHT, AND APPARATUS AND SAMPLE PLATE FOR USE WITH THE SAME

(75) Inventor: Toshihito Kimura, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/236,878

(22) Filed: Sep. 24, 2008

(65) Prior Publication Data
US 2009/0079978 A1    Mar. 26, 2009

(30) Foreign Application Priority Data
Sep. 26, 2007   (JP) .................................. 2007-248671

(51) Int. Cl.
*G01J 3/30*   (2006.01)
(52) U.S. Cl. ........................................................ 356/318
(58) Field of Classification Search .................. 356/301, 356/318, 417, 445
See application file for complete search history.

(56) References Cited

U.S. PATENT DOCUMENTS

| | | | |
|---|---|---|---|
| 7,351,588 B2 * | 4/2008 | Poponin | ......................... 436/171 |
| 2002/0177135 A1 * | 11/2002 | Doung et al. | ..................... 435/6 |
| 2006/0181701 A1 | 8/2006 | Tomaru | |
| 2006/0234396 A1 | 10/2006 | Tomita et al. | |
| 2006/0250613 A1 * | 11/2006 | Demuth et al. | ............... 356/301 |
| 2007/0118936 A1 | 5/2007 | Matsunami | |

FOREIGN PATENT DOCUMENTS

| | | |
|---|---|---|
| JP | 10-090169 A | 4/1998 |
| JP | 2003-294631 A | 10/2003 |
| WO | 93/14391 A1 | 7/1993 |
| WO | 94/28396 A1 | 12/1994 |
| WO | 98/16814 A1 | 4/1998 |

OTHER PUBLICATIONS

Douglas Magde, et al., "Fluorescence Correlation Spectroscopy. II. An Experimental Realization," Biopolymers, 1974, p. 29-61, vol. 13.

(Continued)

*Primary Examiner* — Tarifur Chowdhury
*Assistant Examiner* — Abdullahi Nur
(74) *Attorney, Agent, or Firm* — Sughrue Mion, PLLC

(57) ABSTRACT

A molecular analysis light detection apparatus is formed by: a sample plate provided with an enhancing member which is disposed at a small predetermined area of a sample contact surface contacting with a sample containing a substance to be analyzed and which generates an enhancing field for enhancing light generated from the substance to be analyzed at the predetermined area relative to the light at other areas of the sample contact surface when predetermined excitation light is applied; an excitation-light applying optical system for applying the excitation light to an illumination area which contains the predetermined area of the sample contact surface provided with the enhancing member and which is larger than the predetermined area; and a signal detector unit for detecting fluctuation of the light, which is enhanced by the enhancing field, generated from the substance to be analyzed.

15 Claims, 14 Drawing Sheets

OTHER PUBLICATIONS

Tammy E. Starr, et al., "Local Diffusion and Concentration of IgG near Planar Membranes: Measurement by Total Internal Reflection with Fluorescence Correlation Spectroscopy," Journal of Physical Chemistry, 2002, p. 2365-2371, vol. 106.

Makio Tokunaga, et al., "Single Molecule Imaging of Fluorophores and Enzymatic Reactions Achieved by Objective-Type Total Internal Reflection Fluorescence Microscopy," Biochemical and Biophysical Research Communications, 1997, p. 47-53, vol. 235.

Fluorescence Correlation Spectroscopy—An Introduction to its Concepts and Applications, Petra Schwille and Elke Haustein, Experimental Biophysics Group, pp. 1-33, May 18, 2004.

Dynamics of Fluorescence Marker Concentration As a Probe of Mobility, D. E. Koppel, D. Axelrod, J. Schlessinger, E. L. Elson, and W. W. Webb, Biophysical Journal, vol. 16, 1976, pp. 1315-1329.

* cited by examiner

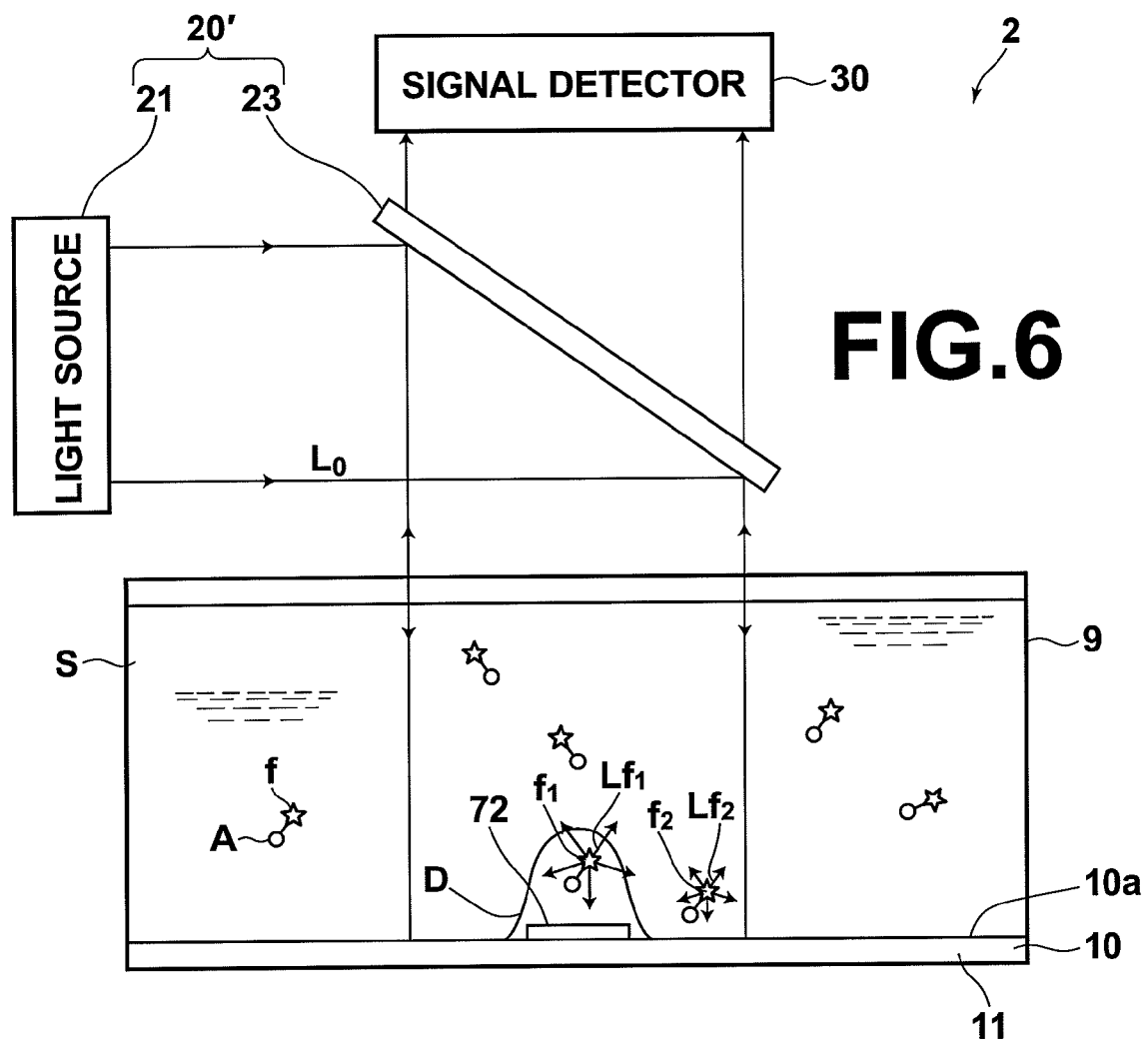

METHOD FOR DETECTING MOLECULAR ANALYSIS LIGHT, AND APPARATUS AND SAMPLE PLATE FOR USE WITH THE SAME

BACKGROUND OF THE INVENTION

1. Field of the Invention

The present invention relates to a molecular analysis light detection method, such as a molecular fluorescence detection method such as fluorescence correlation spectroscopy or fluorescence intensity distribution analysis for detecting behavior of a substance to be analyzed labeled with a fluorescent label contained in a sample, or Raman spectroscopy for spectroscopically analyzing Raman scattering light from a substance to be analyzed. The present invention also relates to a molecular analysis light detection apparatus for use with the method, and a sample plate.

2. Description of the Related Art

Conventionally, apparatuses for detecting the number and/or mobility of particles or molecules that emit fluorescence by receiving fluorescent signals from a small area and statistically processing the signals have been proposed and used in practice, such as Fluorescence Correlation Spectroscopy (or FCS, see "Fluorescence Correlation Spectroscopy. II. An Experimental Realization", D. Magde et al., Biopolymers, Vol. 13, pp. 29-61, 1974) and Fluorescence Intensity Distribution Analysis (or FIDA, see International Patent Publication No. WO98/16814). For example, a fluorescence correlation spectroscopy system is commercially available from Wako Pure Chemical Industries, Ltd., and a single-molecule fluorescence analysis system is commercially available from Olympus Corporation.

These apparatuses detect changes in fluorescent molecules moving in and out of a small volume (i.e., fluctuation of fluorescent signals). In conventional apparatuses, a confocal laser is used as an optical system for exciting fluorescence, and a confocal microscope is used as an optical system for detecting the fluorescence, wherein the focal spot of laser light emitted from the confocal laser is reduced to as small as one femtoliter, so that only the fluorescence which is emitted when a molecule is moving through the confocal area is detected with a very high sensitivity. Specifically, the focal spot of the laser light for illumination is reduced, an objective lens having a high numerical aperture (NA) is provided for collecting the fluorescence, and a pinhole is provided at a position (image position) that is conjugate with the focal spot position of the objective lens just before a photodetector, wherein an area in the in-plane (x-y) direction is limited by the objective lens, and the detection area in the optical axis direction (z-axis direction) is further limited by the pinhole to achieve the small measurement volume of one femtoliter.

Small molecules move fast and pass through the confocal area quickly, and thus rapid changes are observed in the intensity of the fluorescence signal. In contrast, large molecules move slowly, and thus slow changes are observed in the intensity of the fluorescence signal. A motion velocity of the molecule can be found from the frequency of fluctuation of the intensity of the fluorescence signal using an autocorrelation technique to estimate the size of the molecule.

As described above, the conventional apparatuses need to be provided with a high-NA objective lens. However, since the objective lens with a NA that is high enough to detect the molecular fluorescence in the small volume is very expensive, the entire apparatus becomes expensive.

With the laser illumination, the illumination area in the in-plane direction can sufficiently be reduced by the high-NA objective lens, however, the illumination area in the optical path direction cannot be limited, and fluorescent bodies that moving in and out of the optical axis are excited. Therefore, it is necessary to provide the pinhole to limit the detection area in the z-axis direction.

As a means for solving the problem associated with use of the laser illumination, apparatuses for detecting behavior of molecules according to fluorescence correlation spectroscopy using evanescent illumination, which excite the fluorescence with an evanescent wave, are disclosed in "Local Diffusion and Concentration of IgG near Planar Membranes: Measurement by Total Internal Reflection with Fluorescence Correlation Spectroscopy", T. E. Starr and N. L. Thompson, Journal of Physical Chemistry B, Vol. 106, pp. 2365-2371, 2002 and Japanese Unexamined Patent Publication No. 2003-294631.

In these apparatuses, an evanescent wave is generated by applying excitation light so that the excitation light is totally reflected at an interface between a sample and a sample contact surface of a plate that contacts with the sample, and the evanescent wave is used as the illumination for exciting the fluorescence. The evanescent wave reaches only within a range of several hundred nanometers from the interface. Therefore, using this evanescent illumination, the depth of the area for exciting the fluorescence along the optical axis direction (z-axis direction) can be limited without providing the pinhole.

Microscope apparatuses that use the evanescent wave as illumination light for detecting fluorescence have been proposed, for example, in "Single Molecule Imaging of Fluorophores and Enzymatic Reactions Achieved by Objective-Type Total Internal Reflection Fluorescence Microscopy", Biochemical and Biophysical Research Communications, Vol. 235, pp. 47-53, 1997 and Japanese Unexamined Patent Publication No. 10(1998)-090169. In these microscope apparatuses, however, sufficient sensitivity for allowing the single-molecule measurement is not obtained.

In either of the above-described apparatuses, an objective lens with a high NA (>0.3) is necessary for the detection system. Since the objective lens having the NA high enough to detect the molecular fluorescence in the small volume is very expensive, the entire apparatus becomes expensive.

This is also the case in apparatuses for analyzing molecular-level behavior of a substance to be analyzed that generates Raman scattering light by detecting the Raman scattering light in a small volume.

SUMMARY OF THE INVENTION

In view of the above-described circumstances, the present invention is directed to providing a molecular analysis light detection method which allows detection of fluorescence from a small measurement area inexpensively and with very high sensitivity. The invention is also directed to providing and a molecular analysis light detection apparatus for use with the method, and a sample plate.

The molecular analysis light detection method of the invention includes: providing a sample plate including an enhancing member, the enhancing member being disposed at a small predetermined area of a sample contact surface contacting with a sample containing a substance to be analyzed, the enhancing member generating an enhancing field when predetermined excitation light is applied, the enhancing field enhancing light generated from the substance to be analyzed at the predetermined area relative to the light at other areas of the sample contact surface; applying the predetermined excitation light to an illumination area, the illumination area containing the predetermined area of the sample contact surface and being larger than the predetermined area; and detecting fluctuation of the light generated from the substance to be analyzed, the light being enhanced by the enhancing field generated by the application of the predetermined excitation light.

The substance to be analyzed contained in the sample may be labeled with a fluorescent label in advance, and in the step of detecting fluctuation of the light generated from the substance to be analyzed, fluctuation of fluorescence emitted from the fluorescent label of the substance to be analyzed may be detected, or fluctuation of Raman scattering light generated from the substance to be analyzed may be detected. That is, the "light generated from the substance to be analyzed" includes not only light generated from the substance to be analyzed itself, but also includes light emitted from the fluorescent material of the label.

The illumination area to which the excitation light is applied is larger than the predetermined area, and is sized to be able to be illuminated without using a lens having a high NA (>0.3), which is expensive.

The molecular analysis light detection apparatus of the invention includes: a sample plate including an enhancing member, the enhancing member being disposed at a small predetermined area of a sample contact surface contacting with a sample containing a substance to be analyzed, the enhancing member generating an enhancing field when predetermined excitation light is applied, the enhancing field enhancing light generated from the substance to be analyzed at the predetermined area relative to the light at other areas of the sample contact surface; an excitation-light applying optical system for applying the predetermined excitation light to an illumination area, the illumination area containing the predetermined area of the sample contact surface and being larger than the predetermined area; and a signal detector unit for detecting fluctuation of the light generated from the substance to be analyzed, the light being enhanced by the enhancing field.

The molecular analysis light detection apparatus of the invention can be used as a molecular fluorescence detection apparatus. In this case, the substance to be analyzed contained in the sample is labeled with a fluorescent label in advance, the excitation-light applying optical system applies the excitation light having a wavelength that excites fluorescence, and the signal detector unit detects the fluorescence. The molecular analysis light detection apparatus of the invention can be used as a Raman spectroscopic analysis apparatus. In this case, the excitation-light applying optical system applies the excitation light having a wavelength that induces Raman scattering from the substance to be analyzed, and the signal detector unit detects the Raman scattering light.

It should be noted that the molecular analysis light detection apparatus of the invention is adaptable to various detection methods in which the label or the substance to be analyzed can emit light, which is not limited to fluorescence or Raman scattering, when exposed to an electromagnetic wave and the signal depends on the intensity of the light.

The sample plate of the invention is for use with the above-described molecular analysis light detection method, in which fluctuation of light generated from a sample containing a substance to be analyzed when predetermined excitation light is applied to the sample is detected, and the sample plate includes: an enhancing member disposed at a small predetermined area of a sample contact surface contacting with the sample, the predetermined area being smaller than an illumination area of the sample contact surface to be illuminated by the excitation light, the enhancing member generating an enhancing field when the predetermined excitation light is applied, the enhancing field enhancing the light generated from the substance to be analyzed at the predetermined area relative to the light at other areas of the sample contact surface.

The "small predetermined area" is sized such that the volume of the enhancing field generated on the area (measurement volume) is as small as several femtoliters. For example, if the measurement volume is one femtoliter and an effective depth of the enhancing field is about 300 nm, then the size of the predetermined area is about 18 µm×18 µm.

The enhancing member may be one that produces an electric field enhancing field on the surface thereof by generating a non-propagating electromagnetic wave, such as surface plasmon or localized plasmon, when exposed to the excitation light. However, the enhancing member may be made of any material that provides the effect of enhancing the light at the area provided with the enhancing member relative to the light at other areas at which no enhancing member is provided.

The enhancing member may be formed by a metal film provided on the predetermined area (aspect (A)).

Alternatively, a thin metal layer may be formed on the sample contact surface, and the enhancing member may be formed by a metal film formed at an area on the thin metal layer corresponding to the predetermined area (aspect (B)).

Further alternatively, a thin metal layer may be formed on the sample contact surface, and the enhancing member may be formed by an inflexible film, which prevents quenching of the light, formed at an area on the thin metal layer corresponding to the predetermined area (aspect (C)).

In the above aspects (A)-(C), the major component of the metal film and/or the thin metal layer may be at least one selected from the group consisting of Au, Ag, Cu, Al, Pt, Ni, Ti and alloys thereof. The "major component" herein is defined as a component that form 90 mass % or more of the metal film and/or the thin metal layer. In the aspect (A), the metal film may be formed by Ag and the metal film may be covered with an Au film. The metal film is not limited to one having a flat surface, and may be formed by arrayed metal microparticles.

Further alternatively, the enhancing member may be formed by a dielectric multilayer provided on the predetermined area (aspect D). In a case where the substrate having the sample contact surface is made of a dielectric material having a refractive index $n_1$, the dielectric multilayer is formed at least by a cavity layer made of a dielectric material having a refractive index $n_3$ and a dielectric spacer layer having a refractive index $n_2$ sandwiched between the cavity layer and the substrate, where $n_2 < n_1, n_3$.

Further alternatively, the enhancing member may be formed by a small metal structure, which has on a surface thereof an uneven pattern having a cycle smaller than a wavelength of the predetermined excitation light, provided on the predetermined area, or may be formed by metal nanorods, each of which has a size smaller than the wavelength of the predetermined excitation light, disposed on the predetermined area. The "uneven pattern having a cycle smaller than a wavelength of the predetermined excitation light" refers to that the average size and average pitch of protruding portions and depressing portions forming the uneven pattern are smaller than the wavelength of the excitation light. The depressing portions may or may not be provided with the metal. The "metal nanorod" refers to a rod-like metal nanoparticle having different minor and major axis lengths. Similarly to the metal film, the major component of the small metal structure and the metal nanorod may be at least one selected from the group consisting of Au, Ag, Cu, Al, Pt, Ni, Ti and alloys thereof.

The number of the predetermined area provided at the sample contact surface may be one or more than one. If more than one predetermined areas are provided, the predetermined areas may have sizes different from each other. Further, at least one of the predetermined areas may have a binding film, which binds specifically to the substance to be analyzed, fixed thereon, and the other of the predetermined areas may have no binding film fixed thereon.

The inflexible film used in the aspect (C) may be made of $SiO_2$ or a polymer. The term "inflexible" herein refers to that the film is rigid enough that it does not deform to an extent that the thickness thereof is changed as long as the sample plate is used in a normal state. If the inflexible film made of a polymer is applied, a hydrophilic linker which binds to a specific substance may be formed on the inflexible film. The thickness of the inflexible film may range from 10 nm to 100 nm.

BRIEF DESCRIPTION OF THE DRAWINGS

FIG. 6 is a diagram illustrating the schematic configuration of a molecular fluorescence detection apparatus according to a second embodiment of the invention.

DESCRIPTION OF THE PREFERRED EMBODIMENTS

First Embodiment

Figure 1:
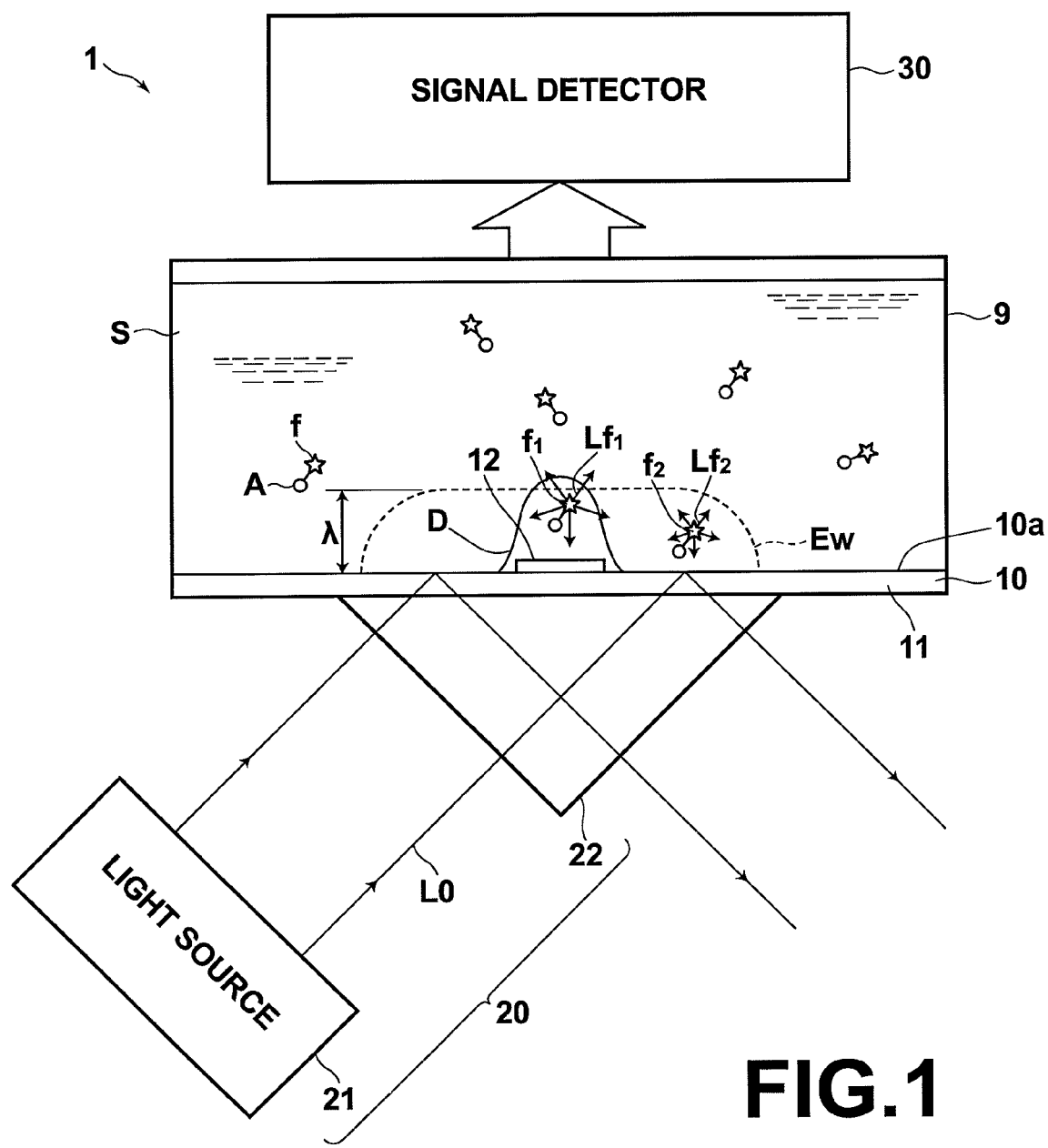
FIG. 1 is a diagram illustrating the schematic configuration of a molecular fluorescence detection apparatus according to a first embodiment of the present invention.

Now, a molecular fluorescence detection method, a molecular fluorescence detection apparatus for use with the method, and a sample plate according to a first embodiment of the molecular analysis light detecting method and apparatus of the invention will be described with reference to the drawings. FIG. 1 is an overall view of the apparatus, and FIGS. 2A-5B show preferred examples of the sample plate. For convenience of explanation, dimensions of components shown in the drawings are not to actual scale.

A molecular fluorescence detection apparatus 1 shown in FIG. 1 includes a sample plate 10, an excitation-light applying optical system 20 and a signal detector unit 30. The sample plate 10 includes an enhancing member 12 provided at a small predetermined area of a sample contact surface 10a, which contacts a sample S containing a substance A to be analyzed being labeled with a fluorescent label f. When the excitation light is applied, the enhancing member 12 enhances light at the small predetermined area relative to the light at other areas of the sample contact surface 10a. The excitation-light applying optical system 20 applies excitation light L0 to an illumination area, which contains the enhancing member 12 and is larger than the predetermined area at which the enhancing member 12 is provided, of the sample contact surface 10a of the sample plate 10 from the side of the sample plate 10 that does not contact with the sample S, such that the excitation light L0 is totally reflected at the sample contact surface 10a to generate an evanescent wave Ew in the illumination area on the sample contact surface 10a. The signal detector unit 30 detects fluctuation of a fluorescent signal that is generated by the fluorescent label f exposed to the evanescent wave Ew.

The excitation-light applying optical system 20 includes a light source 21 formed, for example, by a semiconductor laser (LD) to output the excitation light L0, and a prism 22 that is disposed to contact with the sample plate 10a tone surface thereof. The prism 22 guides the excitation light L0 into the sample plate 10 such that the excitation light L0 is totally reflected at the sample contact surface 10a. The prism 22 contacts with the sample plate 10 via a refractive index-matching oil. The light source 21 is disposed such that the excitation light L0 enters the sample contact surface 10a of the sample plate 10 at a total reflection angle from another surface of the prism 22. A light guiding member may be disposed between the light source 21 and the prism 22, as necessary.

The illumination area on the sample contact surface 10a, to which the excitation light is applied, is larger than the predetermined area at which the enhancing member 12 is provided, and the illumination area is sized to be able to be illuminated using a lens having a NA of 0.3 or less, i.e., without using a lens having a NA higher than 0.3.

The signal detector unit 30 includes a collecting lens to collect fluorescence Lf, a photodetector, such as a photodiode, to detect the fluorescence Lf, an autocorrelator to process a signal from the photodetector using an autocorrelation technique, and the like.

The sample plate 10 is formed by a dielectric plate 11, such as a glass plate, and the enhancing member 12 formed at the small predetermined area on the dielectric plate 11. The small predetermined area is smaller than the illumination area of the excitation light L0 applied to the interface between the sample contact surface 10a and the enhancing member 12 from the side opposite from the side on which the enhancing member 12 is provided. The small area is sized such that a measurement volume, which is defined by an effective volume of an enhancing field generated on the area when the excitation light is applied, of several femtoliters is achieved.

It should be noted that, in this embodiment, a sample holding section 9 to hold the liquid sample S on the sample plate 10 is provided such that the sample plate 10 and the sample holding section 9 form a box-like cell that can hold the liquid sample. In a case where a slight amount of liquid sample which can stay on the sample plate 10 by surface tension is measured, the sample holding section may not be provided.

Figure 2A:
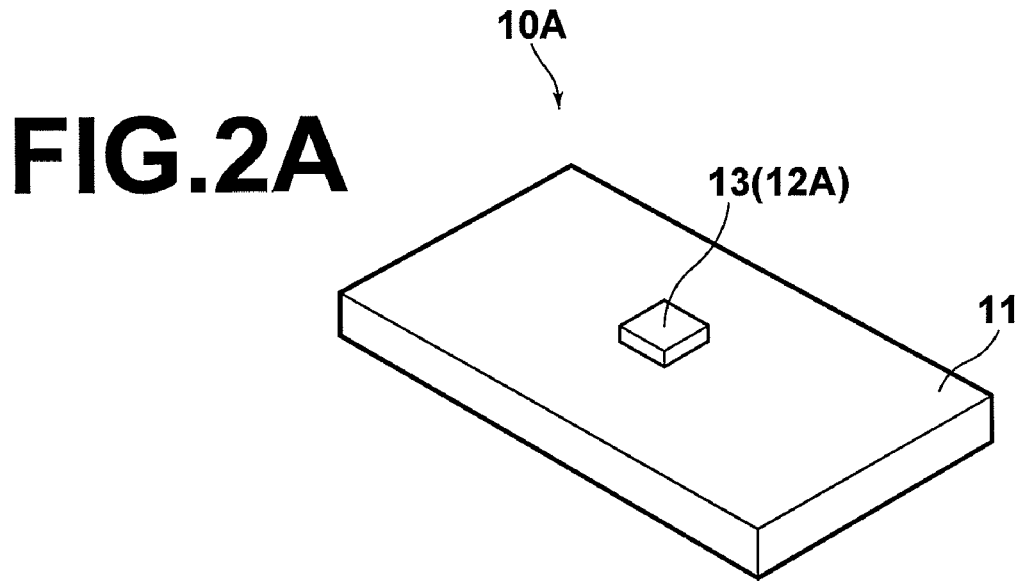
FIG. 2A is a perspective view illustrating a preferred example of a sample plate.

Now, preferred examples 10A-10F of the sample plate 10 are described with reference to FIGS. 2A to 5B. FIGS. 2A, 5A and 5B are perspective views, FIGS. 2B, 3A-3C, 4A and 4B are sectional views, and FIG. 2C is a top view.

Figure 2B:
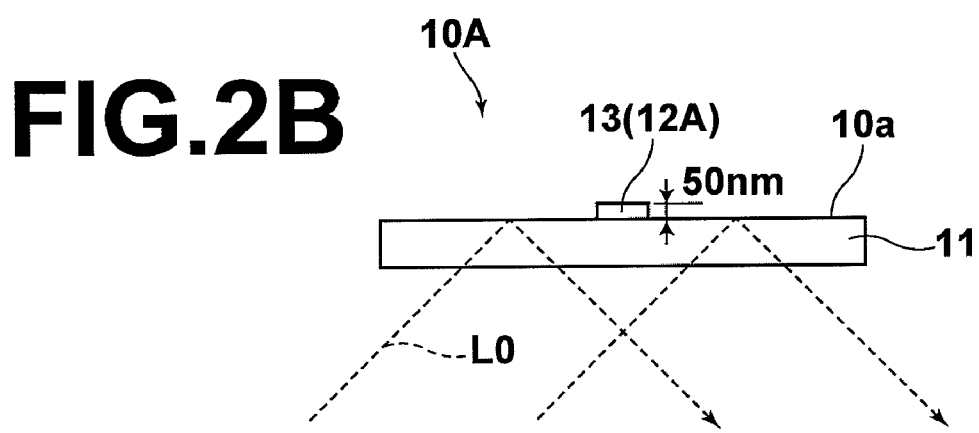
FIG. 2B is a sectional side view of the sample plate shown in FIG. 2A.
Figure 2C:
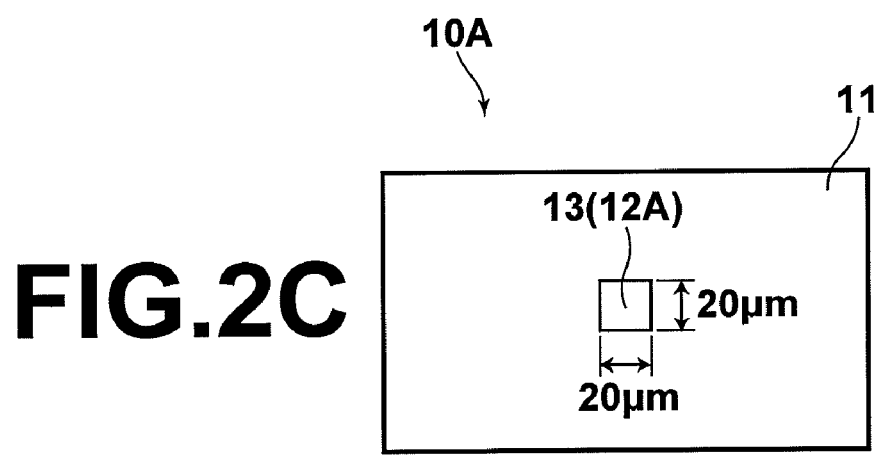
FIG. 2C is a top view of the sample plate shown in FIG. 2A, FIGS. 3A-3C are sectional side views illustrating preferred examples of the sample plate.

The sample plate 10A shown in FIGS. 2A-2C includes a metal film 13 formed at the small predetermined area on one side of the dielectric plate 11, such as a glass plate. The metal film 13 can be formed using a known vapor deposition technique using a mask having an opening in the predetermined area formed on the one side of the plate 11. The metal film 13 can be formed. As shown in FIG. 2B, the predetermined area is smaller than the illumination area of the excitation light L0 (shown by the dashed line in the drawing) applied to the interface between the sample contact surface 10a and the metal film 13 from the side of the plate 11 opposite from the side on which the metal film 13 is provided. As the excitation light L0 is applied to the interface at a total reflection angle, the evanescent wave exudes into the sample contacting with the metal film 13, and surface plasmon is excited at the interface between the metal film and the sample by the evanescent wave. The surface plasmon generates an electric field distribution on the surface of the metal film, and the electric field in the vicinity of the metal surface is enhanced relative to the electric field at other areas. Thus, the light intensity is enhanced within this electric field enhanced area. In this example, the metal film 13 forms an enhancing member 12A.

In the example shown in FIG. 2C, the size of the area at which the metal film 13 is provided is 20 μm×20 μm. The thickness of the metal film 13 may be determined, as appropriate, depending on the material forming the metal film 13 and the wavelength of the excitation light so that the surface plasmon is strongly excited. For example, in a case where the excitation light is laser light having the central wavelength at 780 nm and the metal film is a gold (Au) film, the thickness of the metal film may be 50 nm±5 nm. In this case, the electric field is enhanced by 30% when compared with a case where the Au film is not provided.

Figure 3A:
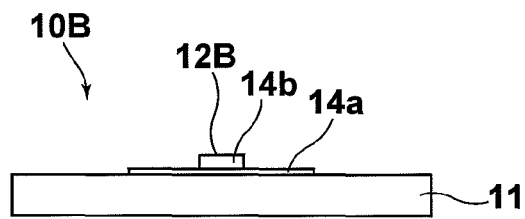

The sample plate 10B shown in FIG. 3A includes a thin metal layer 14a formed at an area, which contains the small predetermined area, of one side of the dielectric plate 11, such as a glass plate, and a metal film 14b formed at a position corresponding to the small predetermined area on the thin metal layer 14a. The electric field enhancing effect by the surface plasmon is greater at the surface of the metal film 14b than at the surface of the thin metal layer 14a. That is, the portion having the thickness increased by the metal film 14b formed on the metal layer 14a forms an enhancing member 12B. The thin metal layer 14a and the metal film 14b may be made of different materials or the same material. For example, in a case where the excitation light is laser light having the central wavelength at 780 nm, and the metal film is a gold (Au) film, the thickness of the thick portion of the metal film may be around 50 nm and the thickness of the thin portion may be around 10 nm.

Figure 3B:
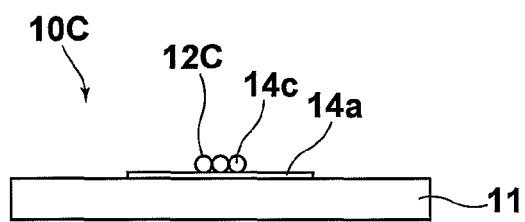

As in a sample plate 10C shown in FIG. 3B, a metal particle layer 14c formed by arrayed metal particles may be formed on the thin metal layer 14a, in stead of the metal film 14b. In this case, the metal particle layer 14c forms an enhancing member 12C. Instead of fixing the arrayed metal microparticles on the thin metal film 14a as shown in FIG. 3B, a single larger metal particle may be fixed on the thin metal film 14a. In this case, the size of the metal particle is around 50 nm-1 um in diameter.

The major component of the metal film and/or the thin metal layer, which is capable to induce the surface plasmon, formed on the dielectric plate 11 may be at least one selected from the group consisting of Au, Ag, Cu, Al, Pt, Ni, Ti and alloys thereof.

Figure 3C:
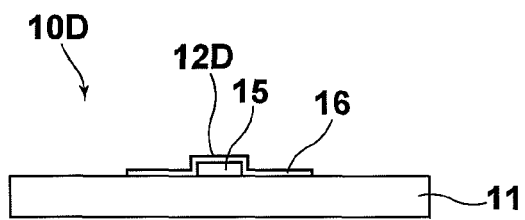

A sample plate 10D shown in FIG. 3C includes an Ag film 15 formed at the small predetermined area on one side of the dielectric plate 11, such as a glass plate, and an Au film 16 formed to cover the Ag film 15. The area at which the Ag film 15 is formed corresponds to the enhancing area, and in this example, an enhancing member 12D is formed by the Ag film 15. The surface plasmon enhancing effect of Ag is larger than that of Au; however, Ag is easy to oxidize. Therefore, by covering the Ag film (having the thickness of 50 nm, for example) with the Au film (having the thickness of 10 nm, for example) in this manner, oxidization of Ag can effectively be prevented.

Figure 4A:
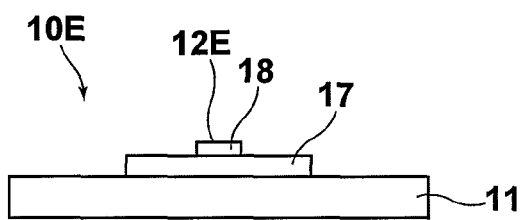
FIGS. 4A and 4B are sectional side views illustrating preferred examples of the sample plate.
Figure 5A:
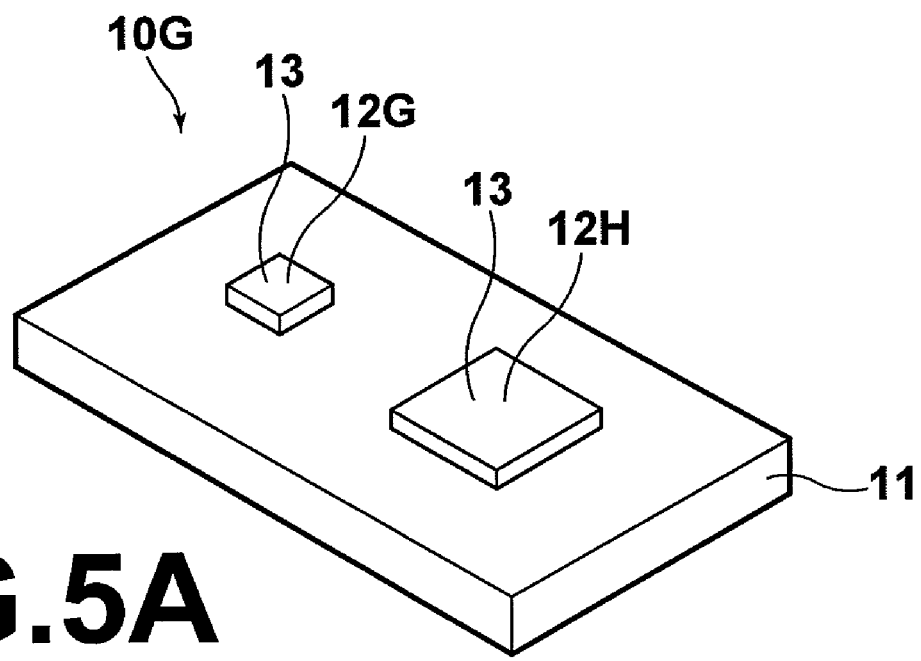
FIGS. 5A and 5B are perspective views illustrating preferred examples of the sample plate.
Figure 5B:
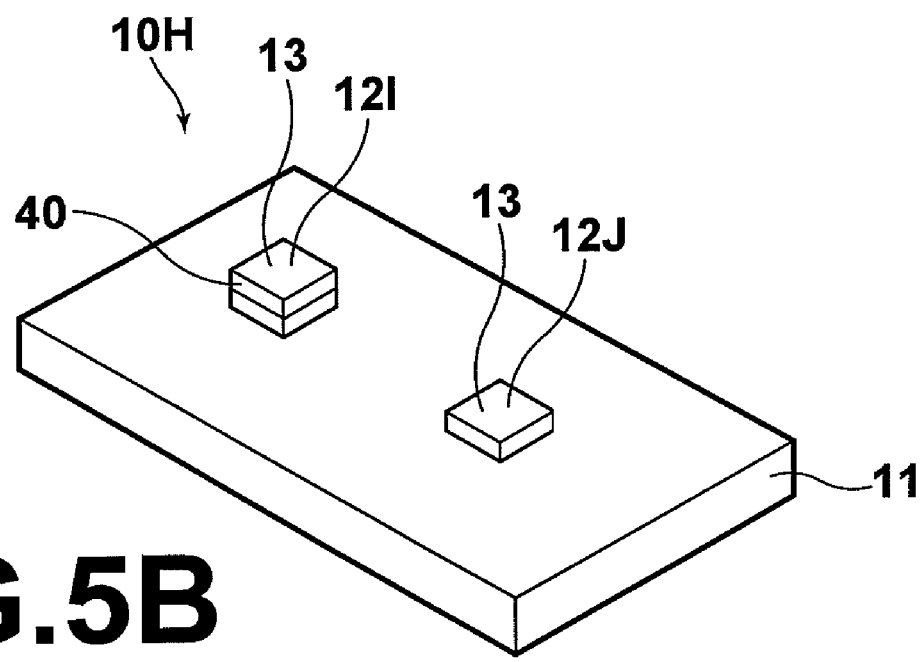

A sample plate 10E shown in FIG. 4A includes a metal film 17 formed at an area containing the small predetermined area on one side of the dielectric plate 11, such as a glass plate, and an inflexible film 18 formed at a position on the metal film 17 corresponding to the small predetermined area. When the fluorescent body in the sample comes too close to the metal film 17, a phenomenon called metal quenching occurs, in which energy excited in the fluorescent body is transferred to the metal before the fluorescence is generated. However, at the position provided with the inflexible film 18, the fluorescent body can be prevented from approaching too close to the metal film and causing the metal quenching. That is, at positions which are not provided with the inflexible film 18, the fluorescence enhancing effect by the surface plasmon electric field is reduced due to the metal quenching. In contrast, at the small predetermined area where the inflexible film 18 is provided, the electric field enhancing effect by the surface plasmon can be ensured to enhance the intensity of the fluorescence. Therefore, the small predetermined area provided with the inflexible film 18 forms an enhancing area where the fluorescence is enhanced relative to the fluorescence at positions without the inflexible film 18, and in this example, the metal film 17 and the inflexible film 18 form an enhancing member 12E.

The thickness of the inflexible film 18 may be in a range from 10 nm to 100 nm, and the reason is as follows. A fluorescent molecule present in the vicinity of a metal experiences quenching due to transfer of the energy to the metal. The degree of the energy transfer decreases inversely proportional to the cube of the distance if the metal is in the form of a plane having semi-infinite thickness; decreases inversely proportional to the fourth power of the distance if the metal is in the form of an infinitely-thin flat plate; or decreases inversely proportional to the sixth power of the distance if the metal is in the form of microparticles. In the case of the metal film, the distance between the metal and the fluorescent molecule may be at least several nanometers, and may optionally be 10 nm or more.

On the other hand, the fluorescent molecule is excited by the evanescent wave which is enhanced by the surface plasmon and exudes to the surface of the metal film. A reachable range (a distance from the surface of the metal film) of the evanescent wave is about the same as the wavelength of the excitation light, and it is known that the electric field intensity thereof attenuates exponentially as the distance from the surface of the metal film increases. Since the larger electric field intensity is desirable for exciting the fluorescent molecule, the distance between the surface of the metal film and the fluorescent molecule may be smaller than 100 nm to carry out effective excitation.

Examples of the material forming the inflexible film having the above-described properties include $SiO_2$ and polymers. However, a protein, or the like, contained in the sample often has a tendency to be nonspecifically adsorbed to a polymer. If this is the case, when an antigen which is specifically adsorbed to an antibody applied on the surface of the inflexible film is detected using a fluorescence technique, for example, a condition similar to this specific adsorption is produced by the nonspecific adsorption, and this will lead to erroneous detection.

Therefore, particularly in a case where the inflexible film made of a polymer is applied, a hydrophilic linker may be formed on the inflexible film to block the protein, or the like, by the linker. In this manner, the protein is kept from being nonspecifically adsorbed to the inflexible film, thereby preventing the above-described erroneous detection. In this case, the antibody, or the like, which should otherwise be placed on the surface of the inflexible film, can be captured on the surface of the inflexible film by being specifically bound with the linker.

Figure 4B:
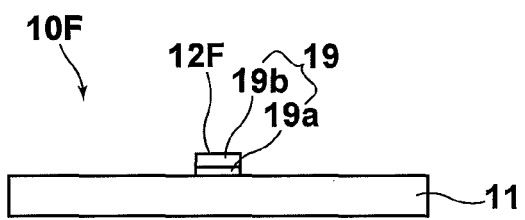

A sample plate 10F shown in FIG. 4B includes a dielectric multilayer 19 provided at the small predetermined area on one side of the dielectric plate 11, such as a glass plate. The multilayer 19 is formed by a spacer layer 19a and a cavity layer 19b, which are disposed in this on from the dielectric plate 11. They are formed by such dielectric materials that, supposing that the plate 11 has a refractive index $n_1$, the spacer layer 19a has a refractive index $n_2$ and the cavity layer 19b has a refractive index $n_3$, the refractive indexes satisfy a relationship: $n_2 < n_1, n_3$.

As the excitation light enters the sample plate 10F provided with the dielectric multilayer 19 from the lower side of the plate 10, at an angle at which the excitation light is totally reflected at the interface between the dielectric plate 11 and the spacer layer 19a, the evanescent electric field is generated, and the evanescent electric field transmits through the spacer layer to excite a guided mode at the cavity layer. Similarly to the surface plasmon, the guided mode generates an electric field distribution at the surface of the cavity layer, and the electric field in the vicinity of the surface of the multilayer is enhanced relative to other areas. The fluorescence intensity is enhanced in this electric field enhanced area, and therefore the dielectric multilayer 19 forms an enhancing member 12F.

Materials of the dielectric layers and thicknesses of the dielectric layers forming the spacer layer 19a and the cavity layer 19b are appropriately selected with taking the wavelength of the excitation light and the wavelength of the fluorescent material into account so that the guided mode is excited at the cavity layer. For example, if the excitation light is a laser having the central wavelength of 780 nm, and a fluorescent dye IRDYe800CW is used as the fluorescent label, the spacer layer may be a magnesium fluoride ($MgF_2$) layer having a thickness of 1000 nm, and the cavity layer may be a titanium dioxide ($TiO_2$) layer having a thickness of 100 nm. As the multiplayer, any other multiplayer that can excite a guided mode, such as those described, for example, in International Patent Publication Nos. WO93/14391 and WO94/28396, can be used.

A sample plate 10G shown in FIG. 5A includes enhancing members 12G and 12H at two predetermined areas having different sizes (areas) on one side of the dielectric plate 11, such as a glass substrate, and the enhancing members 12G and 12H have sizes corresponding to the sizes (areas) of the two predetermined areas. The enhancing members 12G and 12H on the predetermined areas are formed by metal films 13 having different sizes formed on the plate 11. However, the enhancing members 12G and 12H may be formed by any of the above-described means shown in FIGS. 3A-3C and 4A-4B. In order to carry out the detection of the molecular fluorescence with high accuracy, it is necessary to limit the number of molecules of the substance to be analyzed in the measurement volume. Therefore, the measurement volume may be larger to some extent if the concentration of the sample is low, however, if the concentration of the sample is high, a smaller measurement volume is necessary. In the case of the sample plate 10G having the predetermined areas of different sizes, the smaller predetermined area may be used to measure a substance to be analyzed having high concentration, and the larger predetermined area may be used for a substance to be analyzed having low concentration. In this manner, the sample plate 10G can accommodate samples with high to low concentrations, thereby widening the dynamic range. The sizes of the predetermined areas (enhancing areas) provided with the enhancing members may be set as appropriate, such as 20 μm×20 μm and 60 μm×60 μm, respectively.

A sample plate 10H shown in FIG. 5B includes enhancing members 12I and 12J formed at predetermined areas having the same size on one side of the dielectric plate 11, such as a glass plate. The enhancing members 12I and 12J may be formed by any of the above-described means shown in FIGS. 3A-3C and 4A-4B. The one enhancing member 12I is provided with a binding film 40 fixed thereon, which binds specifically to the substance to be analyzed. With the sample plate 10H, the enhancing member 12I can be used as a measurement area and the other enhancing member 12J can be used as a reference measurement area.

It should be noted that the number of the predetermined area (enhancing area) provided with the enhancing member formed on a single dielectric plate is not limited to one or two, and three or more predetermined areas with the enhancing member may be provided on a single dielectric plate. If more than one enhancing areas are provided, the excitation light may be applied to the enhancing areas at once, and separately provided fluorescent detectors may simultaneously detect the fluorescence from these areas. Alternatively, the sample plate and the illumination areas may be relatively moved to apply the excitation light in turn and measure the fluorescence in turn.

Now, a molecular fluorescence detection method using the molecular fluorescence detection apparatus 1 having the above-described structure is described. The description is made on a case where the enhancing member 12 is formed by the metal film 13 provided at the small predetermined area on the dielectric plate 11.

The excitation light L0 emitted from the light source 21 enters, via the prism 22, the sample contact surface 10a (interface) from the side of the sample plate 10 opposite from the sample contact surface 10a at a total reflection angle, and is totally reflected. The illumination by the excitation light L0 generates the evanescent wave Ew (shown by the dashed line in the drawing) at the interface to excite the surface plasmon at the surface of the metal film 13. The surface plasmon generates the electric field distribution D (schematically shown by the solid line in the drawing) on the metal film 13 to form the electric field enhanced area. On the other hand, in the area where the evanescent wave Ew exudes, the fluorescent label f is excited to emit fluorescence. At this time, the intensity of fluorescence Lf1 emitted from a fluorescent label f1 within the electric field enhanced area is enhanced, and the intensity of fluorescence Lf2 emitted from a fluorescent label f2 out of the electric field enhanced area is not enhanced. Further, the fluorescent label f out of the area where the evanescent wave Ew exudes is not excited and does not emit fluorescence. The signal detector unit 30 collects the fluorescence with the collecting lens (not shown) and detects the fluorescence with the photodetector. At this time, the fluorescence may be collected from the fluorescent labels present in a wide range including the electric field enhanced area. By providing, for example, a filter to attenuate the fluorescence between the collecting lens and the photodetector, only the fluorescence with the enhanced intensity can be detected. The fluorescence to be received may be attenuated using other methods such as changing the gain of the light receiving element, or changing the amount of illumination light.

The fluorescent signal detected by the photodetector is processed by the autocorrelator, and the size, or the like, of the molecule can be estimated from the behavior of the molecule labeled with the fluorescent label.

According to the molecular fluorescence detection apparatus and method of this embodiment, only the fluorescent signal emitted from the fluorescent label that moves in and out of the small volume, where the evanescent wave exuding area and the electric field enhanced area overlap with each other, can effectively be detected. This allows highly accurate measurement of the behavior of the fluorescent-labeled molecule.

In order to provide a small measurement volume, the prior art apparatuses use a confocal microscope and a high-NA objective lens, and are configured to collect only the fluorescence within the confocal area. In contrast, in the apparatus of this embodiment, it is not necessary to reduce the detection area as small as the confocal area of the confocal microscope, and therefore does not require a high-NA objective lens. The apparatus of this embodiment can use a typical collecting lens to collect the fluorescence, and therefore can be formed inexpensively. Further, in the prior art apparatuses, the depth of the measurement volume along the optical axis is limited using a pinhole which is disposed just before the detector. In contrast, in the apparatus of this embodiment, the fluorescence excitation area along the optical axis direction can be limit by the evanescent wave exuding area, and therefore the pinhole is not necessary. Without the pinhole, the structure of the apparatus can be simplified, and problems associated with the pinhole, such as decrease in the amount of light passing through the pinhole due to fluctuation of the refractive index of the sample, can be eliminated.

Specific examples of preferred combination of the excitation light source and the fluorescent dye used as the fluorescent label are as follows.

If the light source is formed by combining a LD (LTO21MFO available from Sharp Corporation) or a white LED (E1L5C-AWOA*-04 available from Toyota Gosei Co., Ltd.) having the central wavelength at 743 nm with a band-pass filter available from Andover (740FS10-25), the fluorescent dye to be used may be Cy7 which is excited at 743 nm and emits fluorescence of 767 nm, or Alexa 750 available from Molecular Probe, which is excited at 752 nm and emits fluorescence of 779 nm.

If the light source is formed by combining a LD (LTO24MD available from Sharp Corporation) or a white LED (E1L5C-AWOA*-04 available from Toyota Gosei Co., Ltd.) having the central wavelength at 780 nm with a band-pass filter available from Andover (780FS10-25), the fluorescent dye to be used may be IRDye800 available from LI-COR, which is excited at 787 nm and emits fluorescence of 812 nm.

Second Embodiment

Figure 7A:
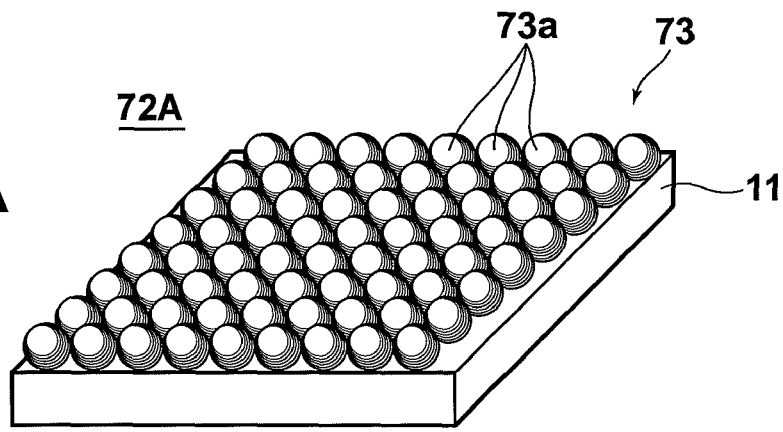
FIGS. 7A and 7B are perspective views illustrating portions of examples of an enhancing member.
Figure 7B:
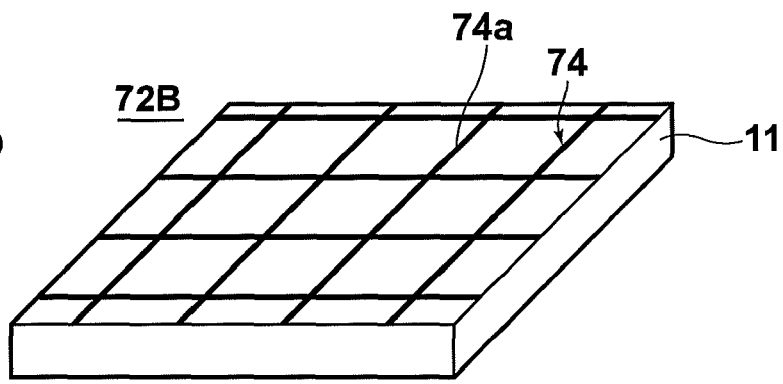
Figure 7C:
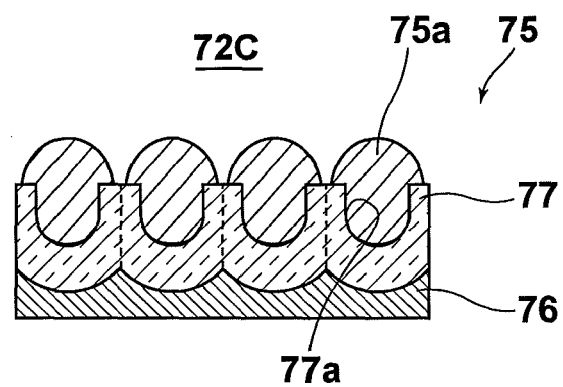
FIG. 7C is a sectional side view illustrating a portion of another example of the enhancing member.
Figure 8:
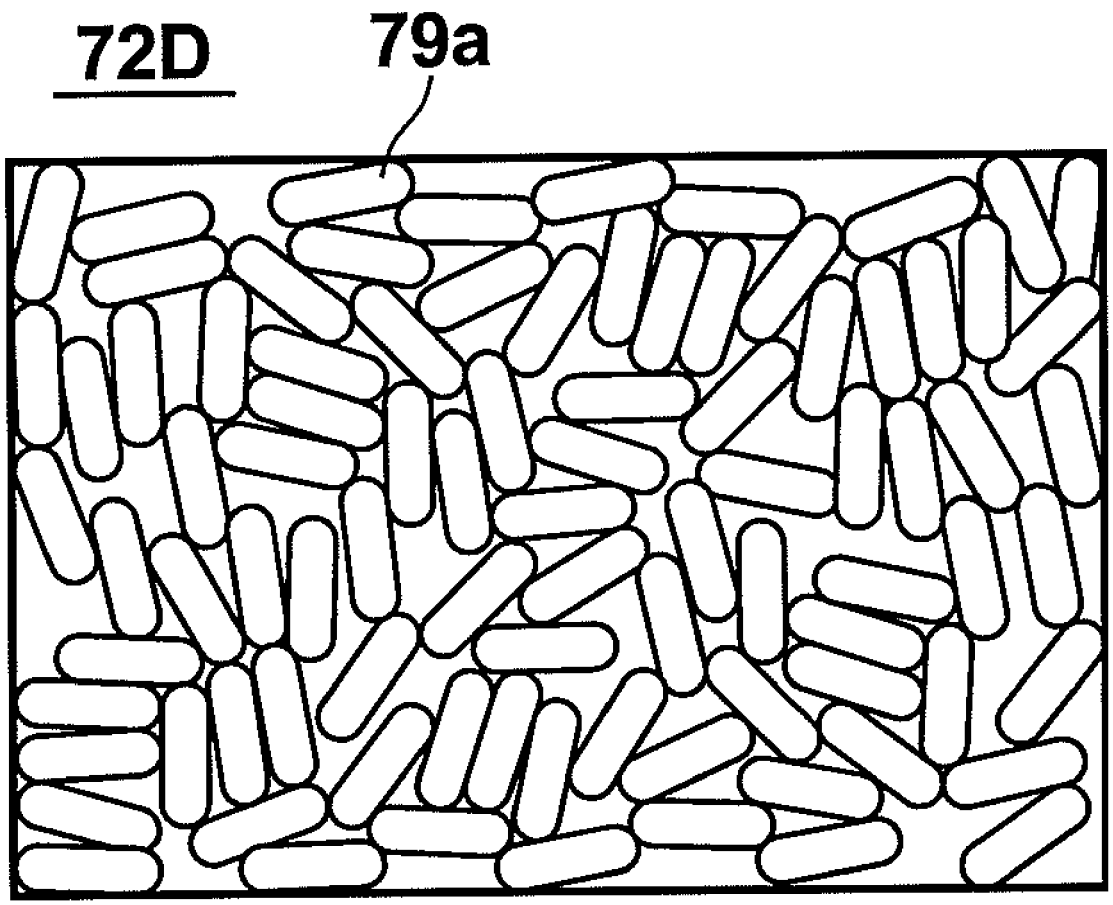
FIG. 8 is a plan view illustrating a portion of yet another example of the enhancing member.

Now, a molecular fluorescence detection method, a molecular fluorescence detection apparatus for use with the method, and a sample plate according to a second embodiment of the invention are described. FIG. 6 is an overall view of the apparatus, and FIGS. 7A-8 show preferred examples of the sample plate in this embodiment. For convenience of explanation, dimensions of components shown in the drawings are not to actual scale. Further, components that are the same as the components in the first embodiment are designated by the same reference symbols.

A molecular fluorescence detection apparatus 2 shown in FIG. 6 includes an enhancing member 72 and an excitation-light applying optical system 20', which are different from the corresponding components in the molecular fluorescence detection apparatus 1 of the first embodiment.

When the enhancing member 72 is illuminated by the excitation light, the enhancing member 72 generates so-called localized plasmon. Similarly to the above-described surface plasmon, the localized plasmon produces the electric field enhancing effect. In the case where this type of enhancing member 72 is provided, it is not necessary to make the excitation light enter at a total reflection angle. Therefore, the excitation-light applying optical system 20' is arranged to apply the excitation light L0 to the sample plate from above.

The excitation-light applying optical system 20' includes the light source 21 formed, for example, by a semiconductor laser (LD) to output the excitation light L0, and a half mirror 23 to reflect and guide the excitation light toward the sample plate. The half mirror 23 reflects the excitation light L0 and transmits the fluorescence.

Now, preferred examples of the sample plate in this embodiment are described with reference to FIGS. 7A-7C and 8. FIGS. 7A-7C and 8 each illustrates a portion of each variation of the enhancing member 72 provided at the small predetermined area of the sample plate, where FIGS. 7A and 7B are perspective views, FIG. 7C is a sectional view, and FIG. 8 is a plan view.

When the enhancing member provided at the small predetermined area is illuminated by the excitation light, the enhancing member generates the localized plasmon to generate the enhancing field. The enhancing member can be formed by a small metal structure having on the surface a non-flat structure which is smaller than the wavelength of the excitation light L0, or multiple metal nanorods which have a size smaller than the wavelength of the excitation light L0.

An enhancing member 72A shown in FIG. 7A is formed by a small metal structure 73, which is formed by multiple metal particles 73a arrayed and fixed on the predetermined area of the dielectric plate 11. The pattern in which the metal particles 73a are arrayed may be designed as appropriate, however, it is preferred that the metal particles 73a are arrayed substantially regularly. In this structure, the average diameter and pitch of the metal particles 73a are designed to be smaller than the wavelength of the excitation light L0.

An enhancing member 72B shown in FIG. 7B is formed by a small metal structure 74, which is formed by a patterned metal layer with thin metal lines 74a formed in a lattice-like pattern, provided on the dielectric plate 11. The pattern of the patterned metal layer may be designed as appropriate, and it is preferred that the pattern is substantially regular. In this structure, the average line width and pitch of the thin metal lines 74a are designed to be smaller than the wavelength of the excitation light L0.

An enhancing member 72C shown in FIG. 7C is formed by a small metal structure 75, which is formed by multiple mushroom-like metal pieces 75a grown in small holes 77a of a metal oxide body 77. The small holes 77a are formed through an anodization process of a metal 76, such as Al. The small metal structure 75 can be obtained by partially anodizing a metal body (such as Al) to form a metal oxide body (such as $Al_2O_3$), and growing the metal pieces 75a by plating or the like in the small holes 77a of the metal oxide body 77 formed through the anodization process.

In the example shown in FIG. 7C, the head portion of each mushroom-like metal piece 75a has a particle-like shape, and thus forms a structure similar to arrayed metal microparticles on the surface of the sample plate. In this structure, the head portions of the mushroom-like metal pieces 75a are protruding portions, and the average diameter and pitch of the protruding portions are designed to be smaller than the wavelength of the excitation light L0.

It should be noted that, besides the above-described examples of the enhancing member, various forms of small metal structures, such as one using a small structure obtained by anodizing a metal body disclosed, for example, in U.S. Patent Application Publication Nos. 20060234396 and 20060181701, can be used as the enhancing member.

The enhancing member may be formed by a metal layer having a roughened surface. An example of the surface roughening method is an electrochemical method utilizing redox, or the like.

An enhancing member 72D shown in FIG. 8 is formed by multiple metal nanorods 79a placed on the sample plate. Each metal nanorod has a minor axis length of about 3 nm-50 nm and a major axis length of about 25 nm-1000 nm, and the major axis length is smaller than the wavelength of the excitation light. Description about the metal nanorod is found, for example, in U.S. Patent Application Publication No. 20070118936.

The major component of the small metal structure or the metal nanorods may be at least one selected from the group consisting of Au, Ag, Cu, Al, Pt, Ni, Ti and alloys thereof.

Now, a molecular fluorescence detection method using the molecular fluorescence detection apparatus 2 having the above-described structure is described.

The excitation light L0 emitted from the light source 21 is reflected by the half mirror 23 and enters the sample contact surface 10a of the sample plate 10. The area illuminated by the excitation light L0 contains the predetermined area and is larger than the predetermined area where the enhancing member 72 is provided. The illumination by the excitation light excites the localized plasmon at the surface of the enhancing member 72. The localized plasmon generates the electric field distribution D (schematically shown by the solid line in the drawing) on the enhancing member 72 to form the electric field enhanced area. On the other hand, in the area in the sample illuminated by the excitation light L0, the fluorescent label f is excited to emit fluorescence. At this time, the intensity of fluorescence Lf1 emitted from a fluorescent label f1 within the electric field enhanced area is enhanced, and the intensity of fluorescence Lf2 emitted from a fluorescent label f2 out of the electric field enhanced area is not enhanced. The signal detector unit 30 collects the fluorescence with the collecting lens (not shown) and detects the fluorescence with the photodetector. At this time, the fluorescence may be collected from the fluorescent labels present in a wide range including the electric field enhanced area. By providing, for example, a filter to attenuate the fluorescence between the collecting lens and the photodetector, only the fluorescence with the enhanced intensity can be detected.

According to the molecular fluorescence detection apparatus and method of this embodiment, only the fluorescent signal emitted from the fluorescent label that moves in and out of the electric field enhanced area can effectively be detected. This allows highly accurate measurement of the behavior of the fluorescent-labeled molecule, and thus the same effect as that of the first embodiment can be provided.

Third Embodiment

Now, a molecular fluorescence detection method and a molecular fluorescence detection apparatus 3 according to a third embodiment of the invention are described with reference to FIGS. 9-11, where components that are the same as the components in the first embodiment are designated by the same reference symbols.

Figure 9:
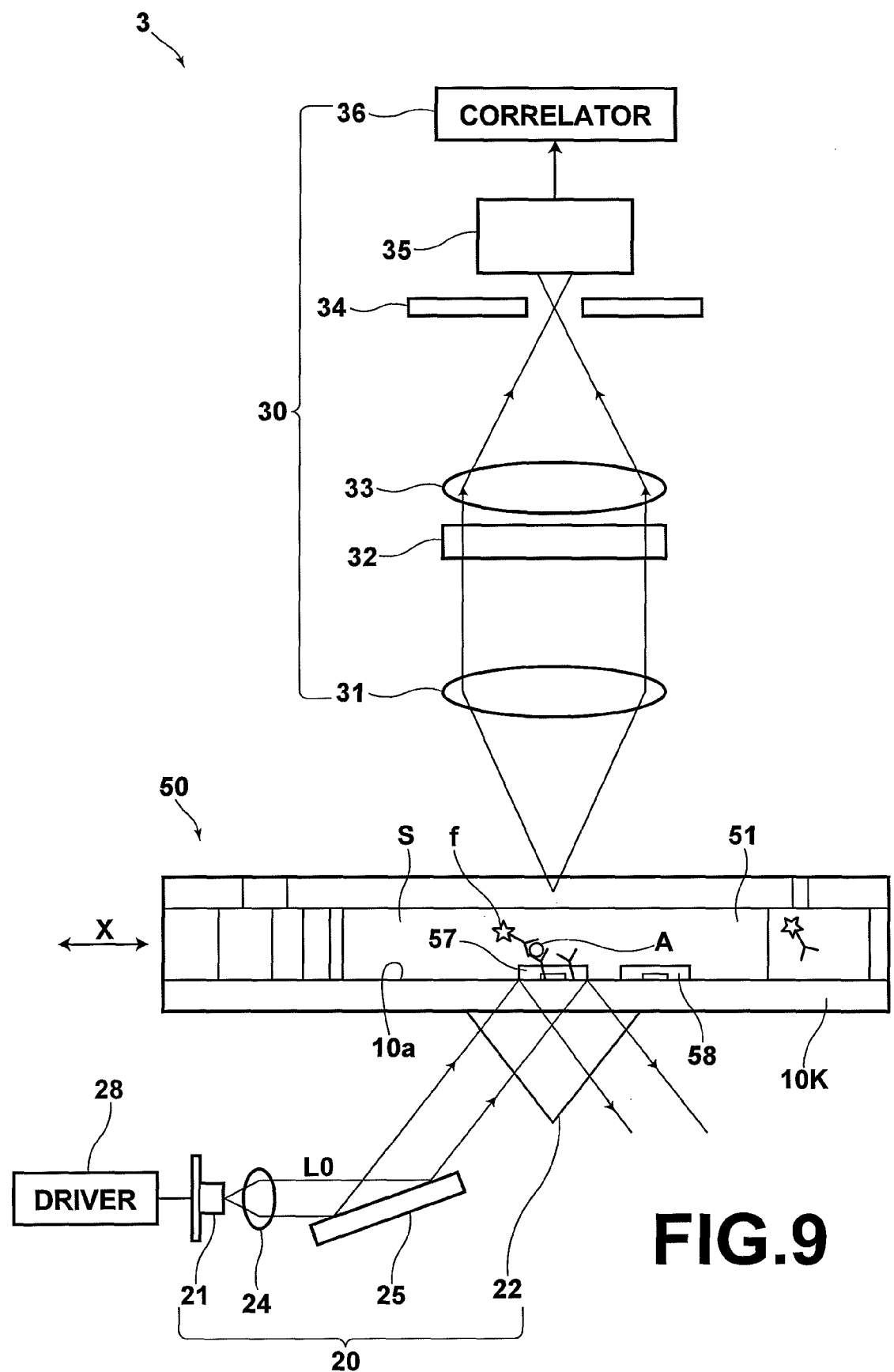
FIG. 9 is a diagram illustrating the schematic configuration of a molecular fluorescence detection apparatus according to a third embodiment of the invention.

The molecular fluorescence detection apparatus 3 shown in FIG. 9 includes a sample cell 50, the excitation-light applying optical system 20 and the signal detector unit 30. The sample cell 50 includes a liquid sample S containing a substance A to be analyzed labeled with the fluorescent label f, a sample contact surface 10a to contact with the sample S, and a flow path 51 through which the liquid sample S flows. The excitation-light applying optical system 20 applies the excitation light L0 to the sample contact surface 10a of the sample cell 50 such that the excitation light L0 is totally reflected at the surface 10a. The signal detector unit 30 detects the fluorescence Lf emitted by the fluorescent label f, which is excited by the evanescent wave exuding from the interface between the sample contact surface 10a and the sample S due to the totally reflected excitation light L0.

The excitation-light applying optical system 20 includes the light source 21 formed by a semiconductor laser (LD) to output the excitation light L0, and the prism 22 that is disposed to contact with the sample plate 10 at one surface thereof, and further includes a light guiding member formed by a lens 24 and a mirror 25 to collect and direct the excitation light L0 emitted from the light source 21 to one surface of the prism 22, and a driver 28 to drive the semiconductor laser light source 21.

The signal detector unit 30 includes: a collecting lens 31 to collect the fluorescence Lf; a filter 32 to remove scattering light and leaking light of the excitation light L0; a lens 33 to guide the fluorescence toward a detector; a pinhole 34 disposed at the focal spot position of the lens 33; an avalanche photodiode (APD) 35 which is a photodetector to receive the fluorescence passed through the pinhole 34; and an autocorrelator 36 to process the signal from the photodetector using an autocorrelation technique. Since the depth of the measurement volume along the optical axis direction (z-axis direction) can be defined by the evanescent wave exuding area, the pinhole is not essential. However, the fluorescence may be excited at areas other than the evanescent wave exuding area by the scattering light and/or leaking light of the excitation light, and therefore, the limitation of the detection area along the z-axis direction may be doubled by providing the pinhole.

Figure 10A:
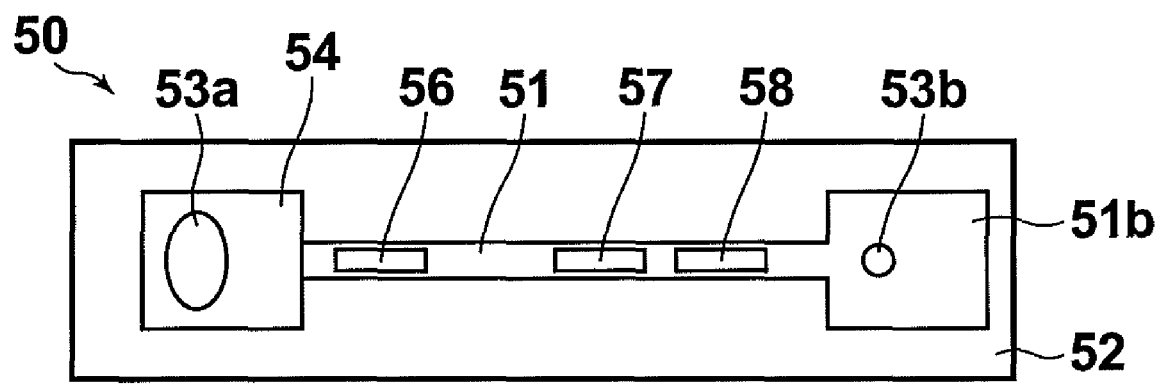
FIG. 10A is a top view of a sample plate for use in the apparatus shown in FIG. 9.
Figure 10B:
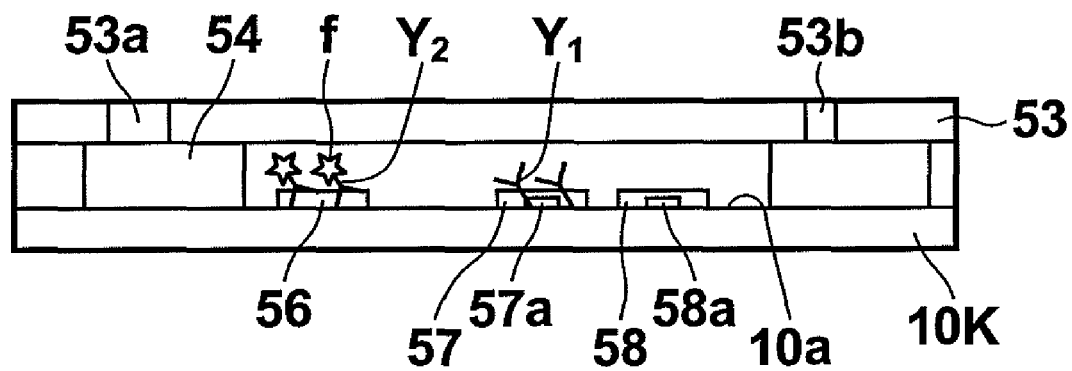
FIG. 10B is a sectional side view of the sample plate.
Figure 11:
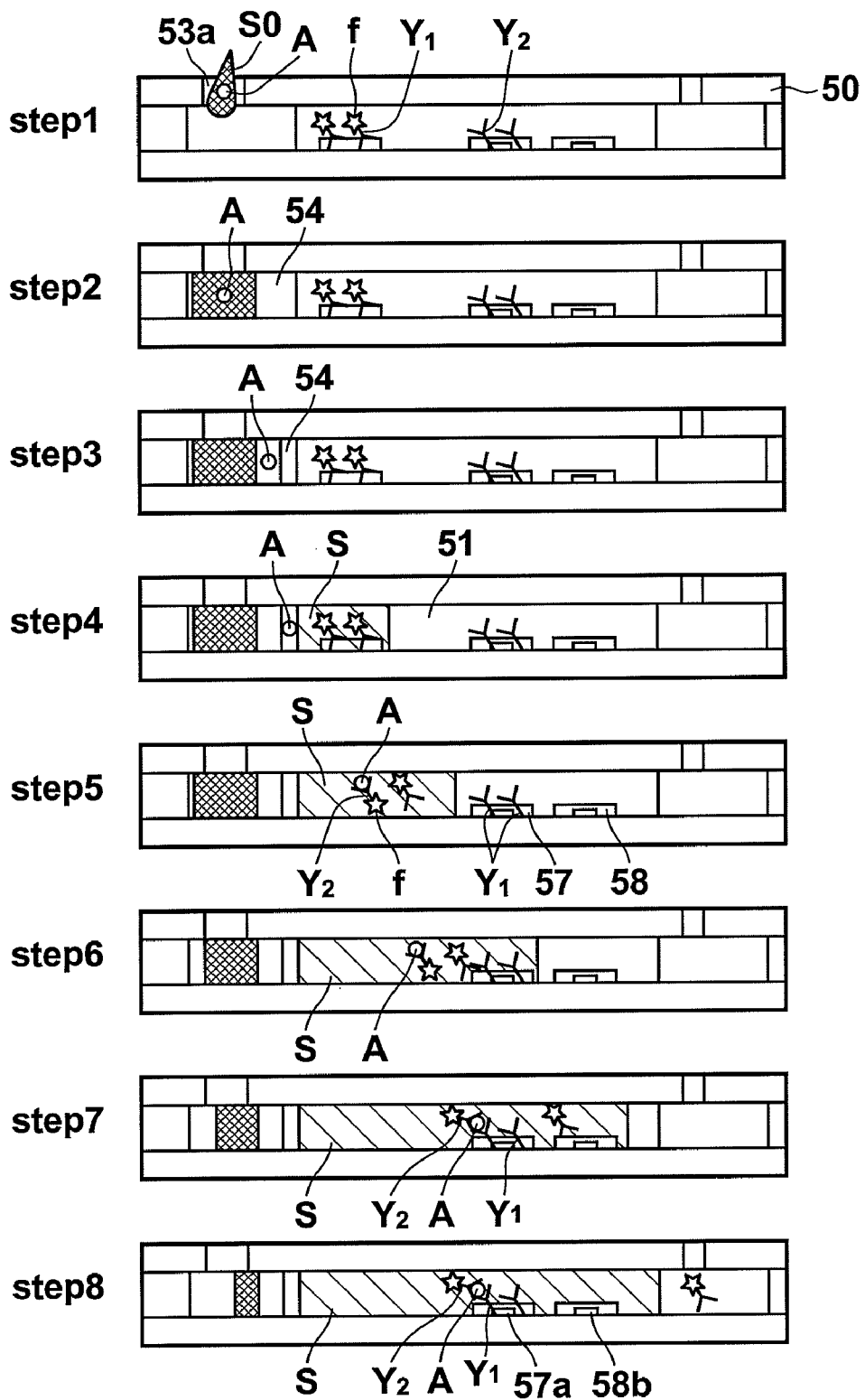
FIG. 11 illustrates a flow of a process in which a sample is injected through an injection port of a sample cell and an antigen binds to a primary antibody.

FIG. 10A is a plan view illustrating the structure of the sample cell 50, and FIG. 10B is a sectional side view of the sample cell 50. The sample cell 50 includes: a sample plate 10K having the sample contact surface 10a to contact with the sample S according to one embodiment of the invention; a spacer 52 to hold the liquid sample S on the sample plate 10K and form the flow path 51 for the liquid sample S; and an upper plate 53 formed by a glass plate provided with an injection port 53*a* and a discharge port 53*b* through which the sample S is injected and discharged. A membrane filter 54 is provided at a portion connecting the injection port 53*a* to the flow path 51. A waste liquid reservoir 51*b* is formed at a portion connecting the flow path 51 to the discharge port 53*b* downstream. Before the sample is charged, a labeled secondary antibody adsorbing area 56 to which a secondary antibody Y2 labeled with the fluorescent label f is physically adsorbed, a first measurement area 57 on which a primary antibody Y1 is immobilized, and a second measurement area 58 on which no antibody is immobilized are provided in this order from the upstream side of the flow path 51 on the sample plate 10K. It should be noted that FIG. 9 shows the sample cell 50 after the sample has been injected and the antibody binding to the labeled secondary antibody has flowed out, and therefore the labeled secondary antibody adsorbing area 56 is no longer present.

Au films 57*a* and 58*a* are formed as the enhancing member at the small predetermined areas on the sample contact surface 10*a* corresponding to the first measurement area 57 and the second measurement area 58. Further, the primary antibody Y1 is immobilized on the Au film at the first measurement area 57. Except this point, the first measurement area and the second measurement area have the same structure. The immobilization of the antibody is carried out using an immobilizing film, such as a CM (carboxymethyldextran) film or a SAM film (self-assembled monomolecular film), provided on the metal film. Other examples of the immobilizing film may include a $SiO_2$ film or PS (polystyrene) film, and in particular, an inorganic substance, such as $SiO_2$, is suitable for mass production.

The sample cell 50 is movable in the X-direction relatively to the excitation-light applying optical system 20 and the signal detector unit 30, so that, after the fluorescence has been detected and measured at the first measurement area 57, the second measurement area 58 is moved to the fluorescence detection area to detect the fluorescence from the second measurement area 58.

The principle of a molecular fluorescence detection method using the molecular fluorescence detection apparatus 3 having the above-described structure is the same as the first embodiment, and therefore the detailed description thereof is omitted. This embodiment can also provide the same effect as that of the first embodiment, and therefore the measurement can be carried out with very high accuracy and the apparatus can be formed inexpensively.

Now, a method for finding the concentration of the substance to be analyzed in the sample using the molecular fluorescence detection apparatus 3 and the detection method of the third embodiment is described.

The primary antibody Y1 is immobilized on the first measurement area 57 of the sample plate 10K of this embodiment. Since the antigen labeled with the fluorescent label f, which is the substance A to be analyzed, gradually binds to the primary antibody Y1 to be immobilized on the first measurement area 57, the amount of the antigen moving in and out of the first measurement area 57 gradually decreases. When the antigen has completely bound with the primary antibody Y1 on the first measurement area 57, fluctuation of the fluorescent signal subsides. Therefore, the time at which the antigen A has completely bound with the primary antibody Y1 can be determined by detecting the fluctuation of the fluorescent signal to detect a change (decrease) in the fluctuation. By measuring the amount of the fluorescence from the first measurement area 57 after the binding has been completed, the amount of the antigen in the sample (concentration) can be found. The second measurement area 58 is a reference area, and is used to correct the signal detected from the first measurement area for the background due to the floating fluorescent dye, and the like.

A flow of a process in which blood (whole blood) containing the antigen, which is the substance to be analyzed, is injected through the injection port of the sample cell 50 and the antigen binds to the primary antibody is described with reference to FIG. 11.

Step 1: The blood (whole blood) S0 containing the antigen A, which is the substance to be analyzed, is injected through the injection port 53*a*. The whole blood S0 is represented by the cross hatched area in FIG. 11.

Steps 2-3: The whole blood S0 is filtered by the membrane filter 54, and larger molecules, such as red blood cells and white blood cells, are filtered out.

Step 4: Blood (blood plasma) S from which the blood cells has been removed by the membrane filter 54 exudes into the flow path 51 due to capillary action. The blood plasma S is represented by the non-cross hatched area in FIG. 11.

Step 5: The blood plasma S exuded into the flow path 51 is mixed with the labeled secondary antibody Y2, and the antigen A in the blood plasma binds to the labeled secondary antibody Y2.

Step 6: The blood plasma S gradually flows along the flow path 51 to the discharge port 53*b*.

Step 7: The antigen A binding to the labeled secondary antibody Y2 further binds to the primary antibody Y1 immobilized on the first measurement area 57 to form a so-called sandwich in which the antigen A is sandwiched between the primary antibody Y1 and the secondary antibody Y2.

Step 8: Even if portions of the labeled secondary antibody Y2 which have not bound to the antigen A remain at the labeled secondary antibody adsorbing area, the subsequent blood plasma serves to wash away the labeled secondary antibody which has been physically adsorbed on the plate.

During the steps 1-8 in which the blood is injected through the injection port and the antigen binds to the primary antibody, the excitation-light applying optical system 20 and the signal detector unit 30 are positioned to detect the fluorescent signal from the first measurement area 57 and measure the fluctuation in the fluorescent signal, as shown in FIG. 9. As the blood plasma flows, the fluorescent labels move in and out of the first measurement area 57, and some of them are immobilized. With this, the fluctuation of the detected fluorescent signal gradually decreases. By detecting the fluorescence intensity from the first measurement area 57 when the fluctuation of the fluorescent signal has subsided, the concentration of the antigen can be found. Thereafter, the sample cell 50 is moved along the X-direction to enable detection of the fluorescent signal from the second measurement area, and the fluorescent signal from the second measurement area is detected. The fluorescent signal from the second measurement area is considered to be a signal from the fluorescent dye which has not bound to the antigen and floats in the sample cell 50. Therefore, this signal is used as a reference signal to correct the signal detected from the first measurement area to provide a more accurate result of detection.

In the above-described embodiment, the sample plate substrate is formed by a dielectric plate, and the prism is disposed below the dielectric plate to direct the excitation light under total reflection conditions. However, one surface of the prism may be used as the sample contact surface and the prism may be used as the sample plate substrate.

Modifications to Third Embodiment

Figure 12:
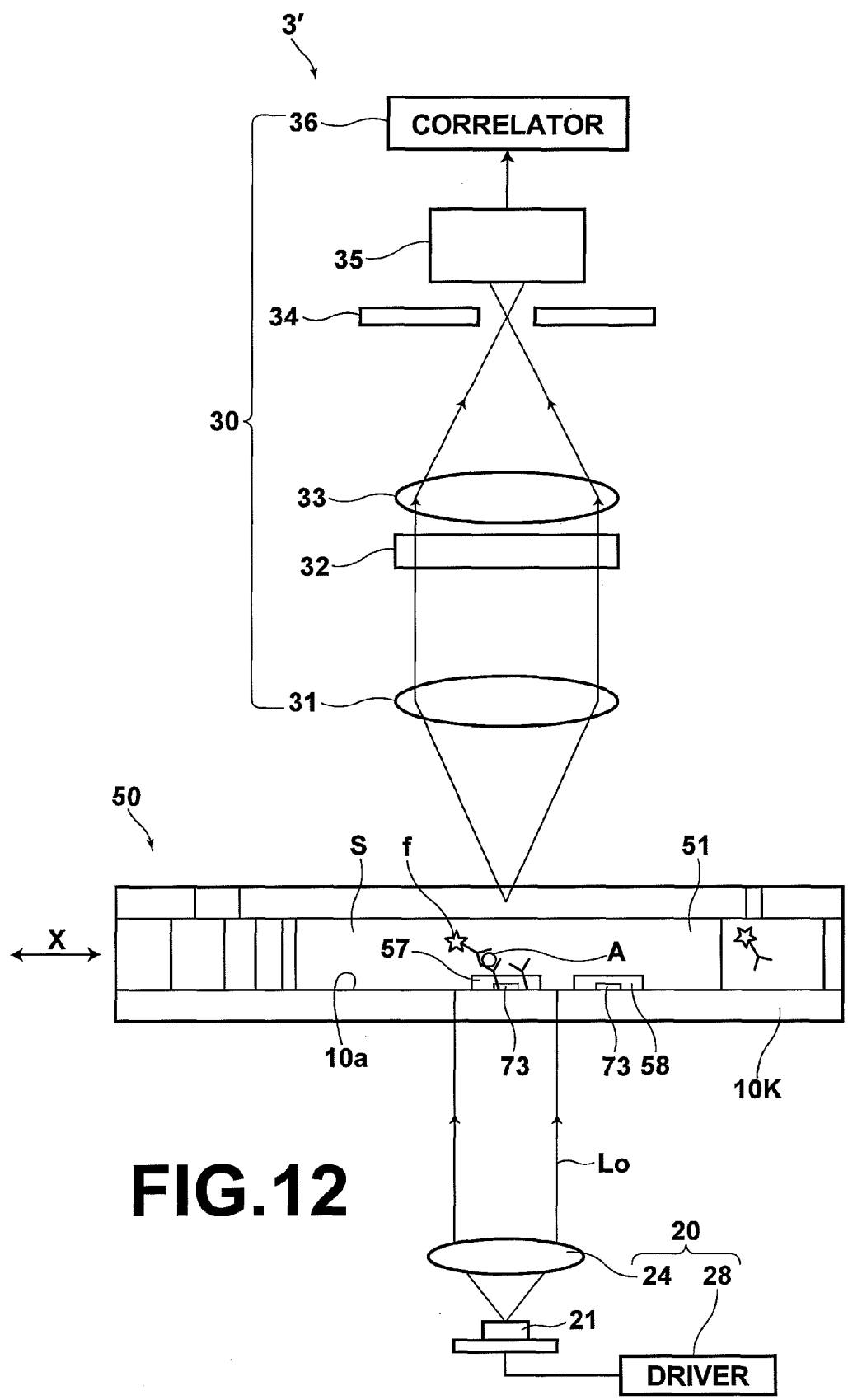
FIG. 12 illustrates a first modification to the third embodiment of the invention.
Figure 13:
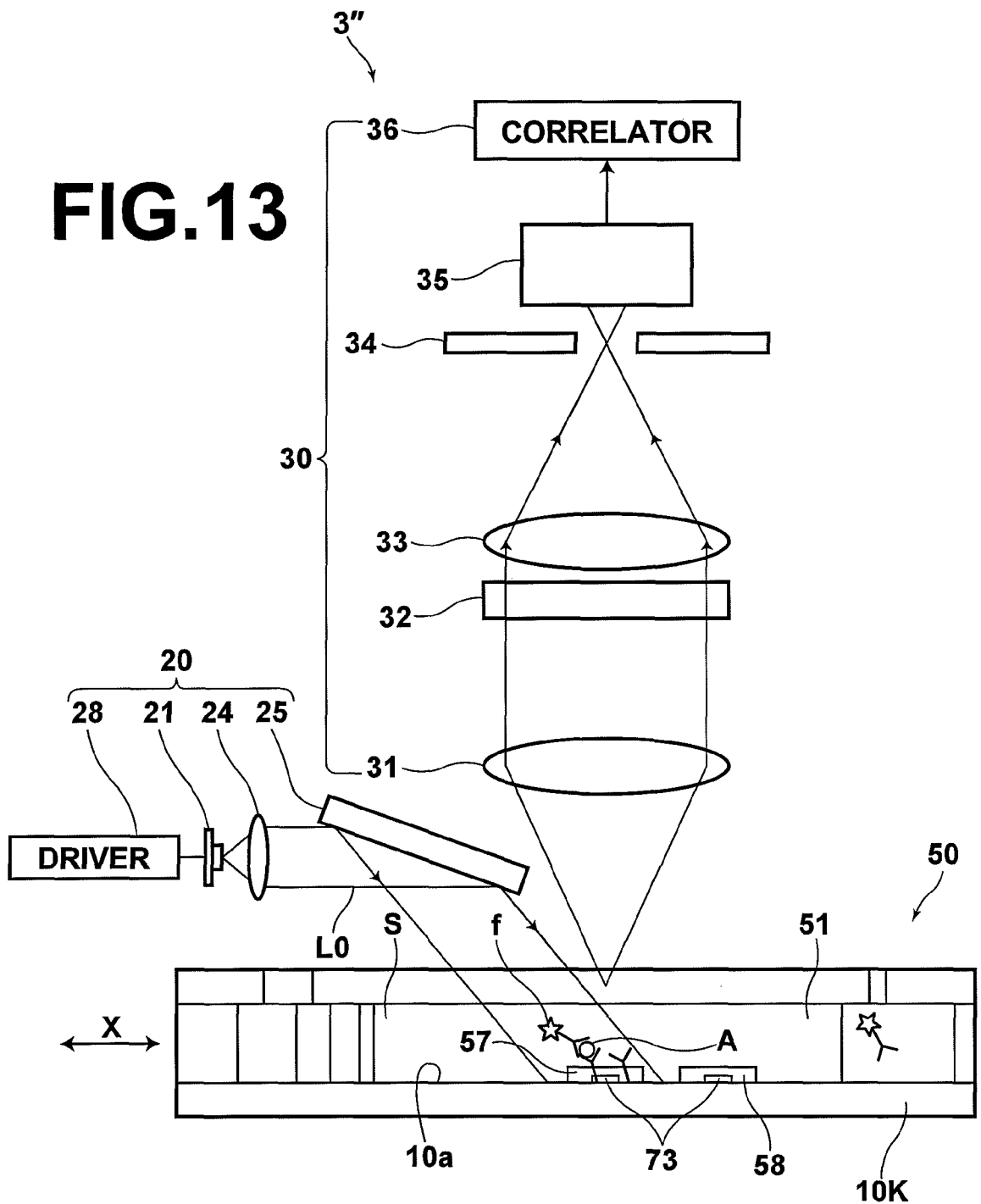
FIG. 13 illustrates a second modification to the third embodiment of the invention.

FIGS. 12 and 13 illustrate modifications to the third embodiment. Small metal structures 73 serving as enhancing members are formed at the small predetermined areas on the sample contact surface 10a corresponding to the first measurement area 57 and the second measurement area 58. As described above in the second embodiment, provision of the small metal structure 73 as the enhancing member allows use of incident light or transmitted light as the excitation light, in stead of the totally reflected light. In this case, the fluorescence is excited not by the evanescent light but by the excitation light L0 itself.

In an apparatus 3' shown in FIG. 12, the excitation-light applying optical system 20 applies the excitation light L0 as transmitted light, not as totally reflected light, to the measurement area from below.

In an apparatus 3" shown in FIG. 13, the excitation-light applying optical system 20 is disposed above the sample cell 50, and applies the excitation light L0 to the measurement area from above the sample cell 50.

In the cases shown in FIGS. 12 and 13, the localized plasmon, which is generated at the small metal structure 73 illuminated by the excitation light, generates the electric field enhancing field, and the fluorescence enhanced at the enhancing field is measured. In these cases, the concentration of the substance to be analyzed can be detected similarly to the third embodiment, and similar effect can be obtained.

Fourth Embodiment

Figure 14:
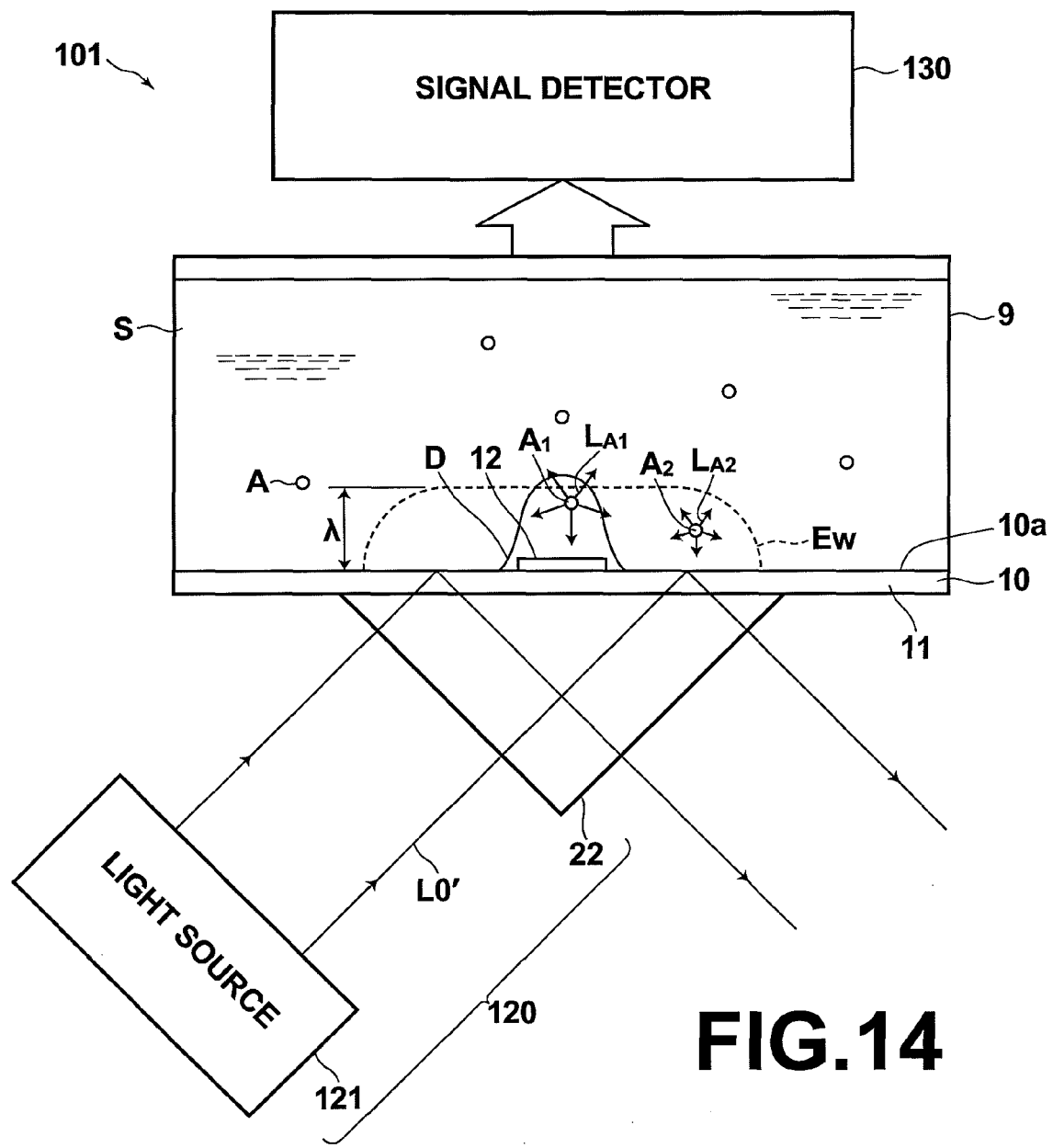
FIG. 14 is a diagram illustrating the schematic configuration of a Raman spectroscopic analysis apparatus according to a fourth embodiment of the invention.

Now, the configuration of Raman spectroscopic analysis method and apparatus according to a fourth embodiment of the molecular analysis light detection method and apparatus of the invention is described. FIG. 14 is an overall view of the apparatus. The structure of the apparatus is substantially the same as the structure of the molecular fluorescence detection apparatus described in the first embodiment. Therefore, the same components are designated by the same reference symbols and are not described in detail.

A Raman spectroscopic analysis apparatus 101 shown in FIG. 14 includes the sample plate 10, an excitation-light applying optical system 120 and a signal detector unit 130. The sample plate 10 includes the enhancing member 12 provided at the small predetermined area of the sample contact surface 10a, which contacts the sample S containing the substance A to be analyzed. When the excitation light is applied, the enhancing member 12 enhances light at the small predetermined area relative to the light at other areas of the sample contact surface 10a. The excitation-light applying optical system 120 applies the excitation light L0 to the illumination area, which contains the enhancing member 12 and is larger than the enhancing member 12, of the sample contact surface 10a of the sample plate 10 from the side of the sample plate 10 that does not contact with the sample S, such that the excitation light L0 is totally reflected at the sample contact surface 10a to generate the evanescent wave Ew in the illumination area on the sample contact surface 10a. The signal detector unit 130 detects fluctuation of Raman scattering light that is generated when the substance A to be analyzed is exposed to the evanescent wave Ew.

The excitation-light applying optical system 120 includes a light source 121 formed, for example, by a semiconductor laser (LD) to output the excitation light L0 of a wavelength which induces the Raman scattering light at the substance A to be analyzed, and the prism 22 that is disposed to contact with the sample plate 10 at one surface thereof.

The signal detector unit 130 includes a collecting lens to collect the Raman scattering light $L_A$, a photodetector to detect the Raman scattering light $L_A$, an autocorrelator to process the signal from the photodetector using an autocorrelation technique, and the like. The photodetector is a spectrometric detector that obtains spectrum of the received light to detect the Raman scattering light and obtain the Raman spectrum.

The sample plate 10 may be any of those described with reference to FIGS. 2A-5B, and can be used in the similar manner as in the apparatus of the first embodiment.

A spectroscopic analysis method using the Raman spectroscopic analysis apparatus 101 of this embodiment is as follows.

The excitation light L0 emitted from the light source 121 enters, via the prism 22, the sample contact surface 10a (interface) from the side of the sample plate 10 opposite from the sample contact surface 10a at a total reflection angle, and is totally reflected. The illumination by the excitation light L0 generates the evanescent wave Ew (shown by the dashed line in the drawing) at the interface to excite the surface plasmon at the surface of the metal film 13. The surface plasmon generates the electric field distribution D (schematically shown by the solid line in the drawing) on the metal film 13 to form the electric field enhanced area. On the other hand, in the area where the evanescent wave Ew exudes, the substance to be analyzed is excited to generate the Raman scattering light. At this time, the intensity of scattering light $L_{A1}$ from a substance $A_1$ to be analyzed within the electric field enhanced area is enhanced, and the intensity of scattering light $L_{A2}$ from a substance $A_2$ to be analyzed out of the electric field enhanced area is not enhanced. Further, portions of the substance to be analyzed out of the exuding area of the evanescent wave Ew are not excited, and do not generate the scattering light. The signal detector unit 130 collects the scattering light with the collecting lens (not shown) and detects the Raman scattering light with the photodetector. Since the Raman scattering light is very weak light, only the enhanced light is effectively detected.

Fifth Embodiment

Figure 15:
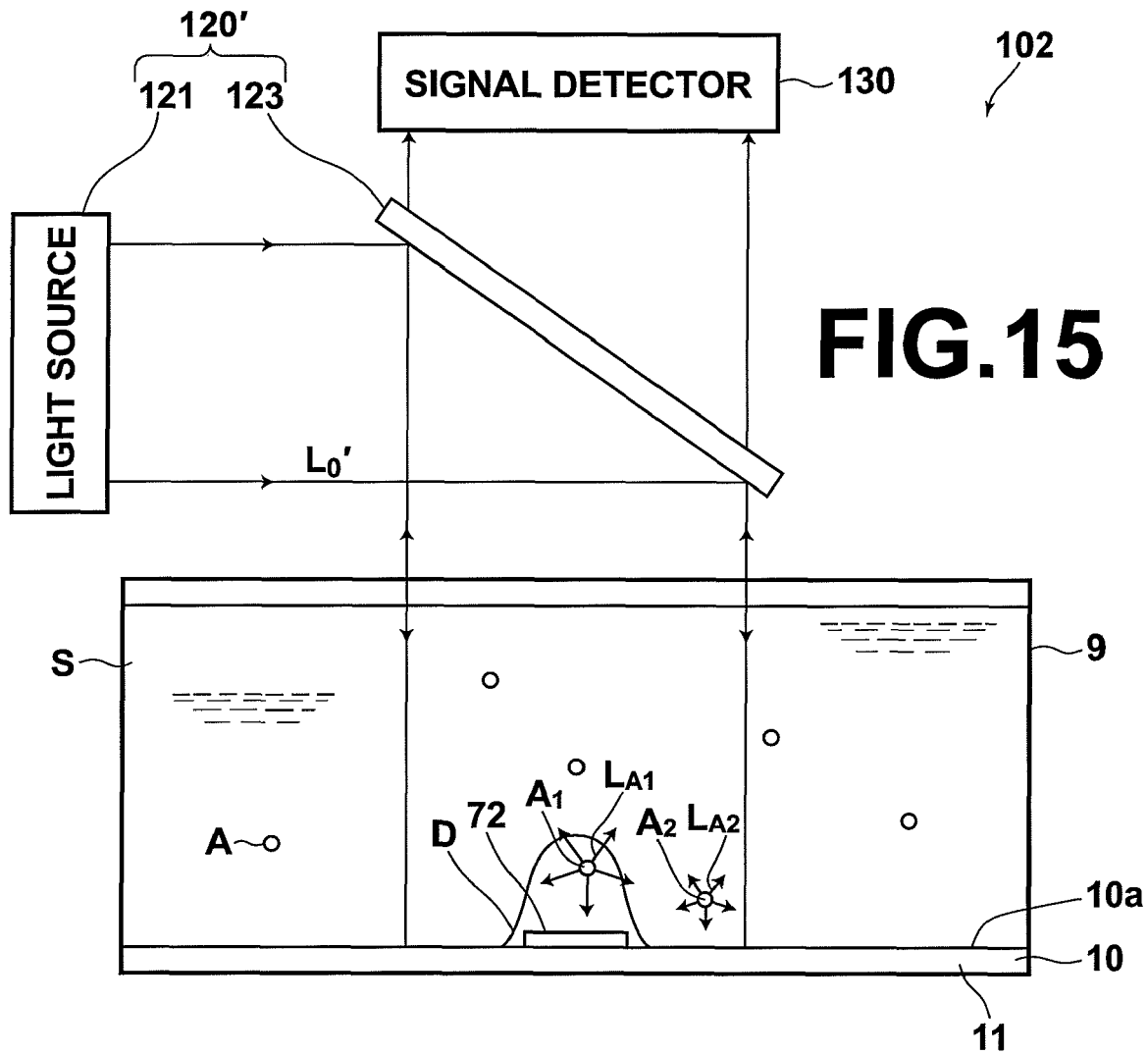
FIG. 15 is a diagram illustrating the schematic configuration of a Raman spectroscopic analysis apparatus according to a fifth embodiment of the invention.

Now, a Raman spectroscopic analysis method and a Raman spectroscopic analysis apparatus, and a sample plate according to the fifth embodiment of the invention are described. FIG. 15 is an overall view of the apparatus. Components which are the same as the above-described embodiment are designated by the same reference symbols.

A Raman spectroscopic analysis apparatus 102 shown in FIG. 15 includes the enhancing member 72 and an excitation-light applying optical system 120', which are different from the corresponding components in the Raman spectroscopic analysis apparatus 101 of the fourth embodiment.

When the enhancing member 72 is illuminated by the excitation light, the enhancing member 72 generates the so-called localized plasmon. Similarly to the above-described surface plasmon, the localized plasmon produces the electric field enhancing effect. In the case where this type of enhancing member 72 is provided, it is not necessary to make the excitation light enter at a total reflection angle. Therefore, the excitation-light applying optical system 120' is arranged to apply the excitation light L0 to the sample plate from above.

The excitation-light applying optical system 120' includes a light source 121 formed, for example, by a semiconductor laser (LD) to output the excitation light L0, and a half mirror 123 to reflect and guide the excitation light toward the sample contact surface of the sample plate 10. The half mirror 123 reflects the excitation light L0 and transmits the Raman scattering light.

The sample plate 10 may be any of those usable with the apparatus of the second embodiment described with reference to FIGS. 7A-7C and 8, which generate the enhancing field based on the localized plasmon.

Now, a molecular fluorescence detection method using the molecular fluorescence detection apparatus 102 having the above-described structure is described.

The excitation light L0 emitted from the light source 121 is reflected by the half mirror 123 and enters the sample contact surface 10a of the sample plate 10. The area illuminated by the excitation light L0 contains the predetermined area where the enhancing member 72 is provided and is larger than the predetermined area. The illumination by the excitation light excites the localized plasmon at the surface of the enhancing member 72. The localized plasmon generates the electric field distribution D (schematically shown by the solid line in the drawing) on the enhancing member 72 to form the electric field enhanced area. On the other hand, within the area in the sample illuminated by the excitation light L0, the Raman scattering light is generated from the substance A to be analyzed. At this time, the intensity of the Raman scattering light $L_{A1}$ from the substance $A_1$ to be analyzed within the electric field enhanced area is enhanced, and the intensity of the Raman scattering light $L_{A2}$ from the substance $A_2$ to be analyzed out of the electric field enhanced area is not enhanced. The signal detector unit 130 collects the Raman scattering light with the collecting lens (not shown) and detects the Raman scattering light with the photodetector. Since the Raman scattering light is very weak light, only the enhanced light is detected.

As described in the fourth and fifth embodiments, the molecular analysis light detection method and apparatus of the invention are applicable not only to fluorescence detection methods and apparatuses but also to Raman spectroscopic analysis methods and apparatuses to provide the same effects.

The molecular analysis light detection method and apparatus of the invention uses a sample plate provided with an enhancing member which is disposed at a small predetermined area of a sample contact surface contacting with a sample containing a substance to be analyzed and generates an enhancing field for enhancing light generated from the substance to be analyzed at the predetermined area relative to the light at other areas of the sample contact surface when predetermined excitation light is applied, so that the light enhanced by the enhancing field is detected. Since the enhancing member is provided only at the small predetermined area, only the light generated at the enhancing field produced on the enhancing member can effectively be detected. That is, the measurement volume is defined by the effective area of the enhancing field. Therefore, even if the detection is carried out over a wider range, only signals with higher intensity can be extracted from the detected light so that only the light which is enhanced in the enhancing field is detected, as a result (to reduce the measurement volume). This can eliminate need of a high-NA objective lens, as in conventional apparatuses, to detect the fluorescence from a reduced small measurement volume. As described previously, a high-NA objective lens is very expensive. Since the method and apparatus of the invention do not necessitate such an expensive objective lens, the apparatus can be formed inexpensively.

The sample plate of the invention is provided with an enhancing member disposed at a small predetermined area of a sample contact surface contacting with the sample, the predetermined area being smaller than an illumination area of the sample contact surface to be illuminated by the excitation light, and the enhancing member generates an enhancing field for enhancing the light generated from the substance to be analyzed at the predetermined area relative to the light at other areas of the sample contact surface when the predetermined excitation light is applied. The above-described effect of the molecular analysis light detection method and apparatus can be obtained by using this sample plate.

If the enhancing member is formed by a metal film provided on the predetermined area, the excitation light is applied under total reflection conditions to generate the surface plasmon at the surface of the predetermined area to enhance the electric field on the surface, thereby enhancing the light within the electric field enhanced area relative to the light in other areas.

The same effect can be obtained with a sample plate in which a thin metal layer is formed on the sample contact surface, and the enhancing member is formed by a metal film formed at an area on the thin metal layer corresponding to the predetermined area.

If a thin metal layer is formed on the sample contact surface, and the enhancing member is formed by an inflexible film, which prevents quenching of the light, formed at an area on the thin metal layer corresponding to the predetermined area, the surface plasmon is generated at the surface of the thin metal layer to enhance the electric field on the surface. In this case, a phenomenon (so-called metal quenching) in which energy excited by the excitation light transfers to the metal before the fluorescence is generated, which occurs when the substance to be analyzed (fluorescent label) comes too close to the thin metal layer, is prevented. As a result, the intensity of the fluorescence at the area provided with the inflexible film can be enhanced relative to the intensity of the fluorescence at areas provided with no inflexible film.

If the major component of the metal film and/or the thin metal layer is at least one selected from the group consisting of Au, Ag, Cu, Al, Pt, Ni, Ti and alloys thereof, the surface plasmon can be induced to generate the electric field distribution at the surface to enhance the fluorescence within the area where the electric field distribution is generated. In particular, Au can enhance the electric field by a factor of about 10 or more and Ag can enhance the electric field by a factor of about 30 or more when compared with a case where the metal film is not provided. If the metal film is made of Ag and the metal film is covered with an Au film, oxidization of Ag can effectively be prevented.

If the enhancing member is formed by a dielectric multilayer provided on the predetermined area, the excitation light applied under total reflection conditions excites a so-called guided mode in the cavity layer to enhance the electric field at the surface of the cavity layer. As a result, the light within this electric field enhanced area can be enhanced.

If the enhancing member is formed by a small metal structure, which has on a surface thereof an uneven pattern having a cycle smaller than a wavelength of the predetermined excitation light, provided on the predetermined area, or is formed by metal nanorods, each of which has a size smaller than the wavelength of the predetermined excitation light, disposed on the predetermined area, the applied excitation light generates the localized plasmon at the surface of the enhancing member to enhance the electric field on the surface. As a result, the light within the electric field enhanced area can be enhanced relative to the light at other areas. If more than one predetermined areas, each of which provided with the enhancing member, are provided on the sample contact surface, measurement can be performed in various manners.

If the predetermined areas have sizes different from each other, the predetermined area having a smaller size may be used for measuring a substance to be analyzed having a high concentration, and the predetermined area having a larger size may be used for measuring a substance to be analyzed having a low concentration. In this manner, the sample plate can accommodate samples with high to low concentrations, thereby widening the dynamic range.

If at least one of the predetermined areas has a binding film, which binds specifically to the substance to be analyzed, fixed thereon and the other of the predetermined areas has no binding film fixed thereon, the one of the predetermined areas may be used as a measurement area and the other may be used as a reference area.

What is claimed is:

1. A molecular analysis light detection method comprising:
    providing a sample plate comprising an enhancing member, the enhancing member being disposed only at a small predetermined area of a sample contact surface contacting with a sample containing a substance to be analyzed, the enhancing member generating an enhancing field when predetermined excitation light is applied, the enhancing field enhancing light generated from the substance to be analyzed at the predetermined area relative to the light at other areas of the sample contact surface;
    applying the predetermined excitation light to an illumination area, the illumination area containing the predetermined area of the sample contact surface and being larger than the predetermined area; and
    receiving the light generated from the substance to be analyzed, the light being enhanced by the enhancing field generated by the application of the predetermined excitation light; and
    detecting at least one of the number and the ease of mobility of the substance to be analyzed that generates light, by processing signals representing the light, using an autocorrelation technique;
    the predetermined small area being small enough to enable processing of the signals representing the light generated within a space defined by the area of the predetermined small area and an effective region of the enhancing field by the autocorrelation technique.

2. The analysis light detection method as claimed in claim 1, wherein the substance to be analyzed is labeled with a fluorescent label in advance, and detecting fluctuation of the light generated from the substance to be analyzed comprises detecting fluctuation of fluorescence emitted from the fluorescent label of the substance to be analyzed.

3. The analysis light detection method as claimed in claim 1, wherein detecting fluctuation of the light generated from the substance to be analyzed comprises detecting fluctuation of Raman scattering light generated from the substance to be analyzed.

4. A sample plate for use with the molecular analysis light detection method as claimed in claim 1 in which the light generated from a sample containing a substance to be analyzed, when predetermined excitation light is applied to the sample, is received, and at least one of the number and the ease of mobility of the substance to be analyzed that generates light, by processing signals representing the light, using an autocorrelation technique, is detected, the sample plate comprising:
    an enhancing member disposed only at a small predetermined area of a sample contact surface contacting with the sample, the predetermined area being smaller than an illumination area of the sample contact surface to be illuminated by the excitation light, the enhancing member generating an enhancing field when the predetermined excitation light is applied, the enhancing field enhancing the light generated from the substance to be analyzed at the predetermined area relative to the light at other areas of the sample contact surface,
    the predetermined small area being small enough to enable processing of the signals representing the light generated within a space defined by the area of the predetermined small area and an effective region of the enhancing field by the autocorrelation technique.

5. The sample plate as claimed in claim 4, wherein the enhancing member comprises a metal film provided on the predetermined area.

6. The sample plate as claimed in claim 5, wherein
    the metal film comprises Ag, and
    the metal film is covered with an Au film.

7. The sample plate as claimed in claim 4, wherein
    a thin metal layer is formed on the sample contact surface, and
    the enhancing member comprises a metal film formed at an area on the thin metal layer corresponding to the predetermined area.

8. The sample plate as claimed in claim 4, wherein
    a thin metal layer is formed on the sample contact surface, and
    the enhancing member comprises an inflexible film formed at an area on the thin metal layer corresponding to the predetermined area, the inflexible film preventing quenching of the light.

9. The sample plate as claimed in claim 4, wherein
    the enhancing member comprises a dielectric multilayer provided on the predetermined area.

10. The sample plate as claimed in claim 4, wherein
    the enhancing member comprises a small metal structure provided on the predetermined area, the small metal structure having an uneven pattern on a surface thereof, the pattern having a cycle smaller than a wavelength of the predetermined excitation light.

11. The sample plate as claimed in claim 4, wherein
    the enhancing member comprises metal nanorods disposed on the predetermined area, each metal nanorod having a size smaller than a wavelength of the predetermined excitation light.

12. The sample plate as claimed in claim 4, wherein
    the predetermined area on the sample contact surface comprises more than one predetermined areas, each predetermined area being provided with the enhancing member.

13. The sample plate as claimed in claim 12, wherein
    the predetermined areas have sizes different from each other.

14. The sample plate as claimed in claim 12, wherein
    at least one of the predetermined areas has a binding film fixed thereon, the binding film binding specifically to the substance to be analyzed, and the other of the predetermined areas has no binding film fixed thereon.

15. A molecular analysis light detection apparatus comprising:
    a sample plate comprising an enhancing member, the enhancing member being disposed only at a small predetermined area of a sample contact surface contacting with a sample containing a substance to be analyzed, the enhancing member generating an enhancing field when predetermined excitation light is applied, the enhancing field enhancing light generated from the substance to be analyzed at the predetermined area relative to the light at other areas of the sample contact surface;

an excitation-light applying optical system for applying the predetermined excitation light to an illumination area, the illumination area containing the predetermined area of the sample contact surface and being larger than the predetermined area; and a signal detector unit for receiving the light generated from the substance to be analyzed, the light being enhanced by the enhancing field and for detecting at least one of the number and the ease of mobility of the substance to be analyzed that generates light, by processing signals representing the light, using an autocorrelation technique, the predetermined small area being small enough to enable processing of the signals representing the light generated within a space defined by the area of the predetermined small area and an effective region of the enhancing field by the autocorrelation technique.

* * * * *